(12) United States Patent
Roe et al.

(10) Patent No.: US 6,433,244 B1
(45) Date of Patent: *Aug. 13, 2002

(54) DISPOSABLE TREATMENT ARTICLE HAVING A RESPONSIVE SYSTEM

(75) Inventors: Donald C. Roe, West Chester; Patrick J. Allen, Cincinnati, both of OH (US); Bruno J. Ehrnsperger, Frankfurt am Main; Mattias Schmidt, Idstein, both of (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/342,785

(22) Filed: Jun. 29, 1999

Related U.S. Application Data

(63) Continuation-in-part of application No. 09/107,561, filed on Jun. 29, 1998, and a continuation-in-part of application No. 09/106,225, filed on Jun. 29, 1998.
(60) Provisional application No. 60/090,993, filed on Jun. 29, 1998.

(51) Int. Cl.[7] .................................................. A61F 13/15
(52) U.S. Cl. .................. 604/361; 604/360; 604/385.01; 604/359; 604/367
(58) Field of Search .............................. 604/380, 359, 604/360, 368, 379, 385.01, 362, 361, 367, 378, 385.101, 358, 385.12; 401/271; 15/208, 209.1, 230, 244.4, 228

(56) References Cited

U.S. PATENT DOCUMENTS 2,127,538 A  8/1938  Seiger ........................ 128/238
2,926,667 A  3/1960  Burger et al. .............. 128/285

(List continued on next page.)

FOREIGN PATENT DOCUMENTS

| EP | 0 612 520 A2 | 8/1994 | ............ A61K/9/52 |
|----|---|---|---|
| EP | 0 804 912 | 11/1997 | ............ A61F/13/15 |
| EP | 0 804 913 | 11/1997 | ............ A61F/13/15 |
| EP | 0 804 914 A1 | 11/1997 | ............ A61F/13/15 |
| EP | 0 804 915 | 11/1997 | ............ A61F/13/15 |
| EP | 0 804 916 | 11/1997 | ............ A61F/13/15 |
| EP | 0 804 917 | 11/1997 | ............ A61F/13/15 |
| EP | 0 806 194 | 11/1997 | ............ A61F/13/15 |
| EP | 0 806 195 | 11/1997 | ............ A61F/13/15 |
| EP | 0 815 818 A1 | 1/1998 | ............ A61F/13/15 |
| EP | 0 815 821 A2 | 1/1998 | ............ A61F/13/15 |
| JP | 10-62369 | 3/1998 | ............ G01N/27/00 |
| JP | 0127758 | 11/1999 | ............ A61F/5/44 |
| WO | WO 92/02005 A | 2/1992 | ............ G08F/8/00 |
| WO | WO 94/24974 | 11/1994 | ............ A61F/13/15 |
| WO | WO 95/00089 | 1/1995 | ............ A61F/13/15 |
| WO | WO 95/00090 | 1/1995 | ............ A61F/13/15 |
| WO | WO 95/32697 | 12/1995 | ............ A61F/13/15 |
| WO | WO 95/32698 | 12/1995 | ............ A61F/13/15 |
| WO | WO 96/20681 | 7/1996 | ............ A61F/13/15 |
| WO | WO 97/16149 | 5/1997 | ............ A61F/13/42 |
| WO | WO 97/24150 | 7/1997 | ............ A61L/15/62 |
| WO | WO 97/32542 | 9/1997 | ............ A61F/2/00 |
| WO | WO 97/42613 | 11/1997 | ............ G08B/21/100 |
| WO | WO 97/45082 | 12/1997 | ............ A61F/13/15 |
| WO | WO 98/18505 | 5/1998 | ............ A61L/15/60 |
| WO | WO 98/22063 | 5/1998 | ............ A61F/13/15 |
| WO | WO 98/29501 | 7/1998 | ............ C08L/1/28 |
| WO | WO 99/07317 | 2/1999 | ............ A61F/13/15 |

*Primary Examiner*—John G. Weiss
*Assistant Examiner*—Jacqueline Stephens
(74) *Attorney, Agent, or Firm*—Jeffrey R. Moore; David M. Weirich; Ken K. Patel

(57) ABSTRACT

Disposable articles for treating objects such as surfaces, devices, persons, contaminants, and the like or for treating substances disposed on, in, or in proximity to such objects having a responsive system. The responsive system may respond continuously or discontinuously. A continuous responsive system of the present invention further includes a feedback control loop. A discontinuous responsive system of the present invention may include either a feedback control loop or an open loop.

34 Claims, 12 Drawing Sheets

U.S. PATENT DOCUMENTS

| | | | |
|---|---|---|---|
| 3,814,101 A | 6/1974 | Kozak | 128/287 |
| 3,881,491 A | 5/1975 | Whyte | 128/287 |
| 3,920,015 A * | 11/1975 | Wortham | 128/284 |
| 3,921,232 A | 11/1975 | Whyte | 5/91 |
| 3,987,792 A | 10/1976 | Hernandez et al. | 128/284 |
| 4,022,211 A | 5/1977 | Timons et al. | 128/287 |
| 4,246,900 A | 1/1981 | Schröder | 128/287 |
| 4,311,479 A | 1/1982 | Fenn et al. | 8/495 |
| 4,356,818 A | 11/1982 | Macias et al. | 128/138 |
| 4,401,712 A | 8/1983 | Morrison | 428/289 |
| 4,636,474 A | 1/1987 | Ogura et al. | 435/291 |
| 4,657,537 A | 4/1987 | Zimmerer | 604/360 |
| 4,681,577 A | 7/1987 | Stern et al. | 604/378 |
| 4,705,050 A | 11/1987 | Markham | 128/749 |
| 4,732,930 A | 3/1988 | Tanaka et al. | 524/742 |
| 4,747,166 A | 5/1988 | Kuntz | 4/144.1 |
| 4,753,645 A | 6/1988 | Johnson | 604/378 |
| 4,754,264 A | 6/1988 | Okada et al. | 340/573 |
| 4,776,331 A | 10/1988 | Simjian | 128/169 |
| 4,778,459 A | 10/1988 | Fuisz | 604/378 |
| 4,787,896 A | 11/1988 | Houghton et al. | 604/385.1 |
| 4,790,836 A | 12/1988 | Brecher | 604/359 |
| 4,796,014 A | 1/1989 | Chia | 340/573 |
| 4,842,593 A | 6/1989 | Jordan et al. | 604/360 |
| 4,981,465 A | 1/1991 | Ballan et al. | 600/32 |
| 5,002,541 A | 3/1991 | Conkling et al. | 604/319 |
| 5,100,933 A | 3/1992 | Tanaka et al. | 523/300 |
| 5,118,607 A | 6/1992 | Bignami et al. | 435/7.1 |
| 5,181,905 A | 1/1993 | Flam | 602/41 |
| 5,264,830 A | 11/1993 | Kline et al. | 340/604 |
| 5,330,459 A | 7/1994 | Lavon et al. | 604/385.1 |
| 5,341,127 A | 8/1994 | Smith | 340/604 |
| 5,342,343 A | 8/1994 | Kitaoka et al. | 604/385.2 |
| 5,416,469 A | 5/1995 | Colling | 340/573 |
| 5,468,236 A | 11/1995 | Everhart et al. | 604/361 |
| 5,520,674 A | 5/1996 | Lavon et al. | 604/385.1 |
| 5,558,655 A | 9/1996 | Jezzi et al. | 604/378 |
| 5,568,128 A * | 10/1996 | Nair | 340/604 |
| 5,582,604 A | 12/1996 | Ahr et al. | 604/385.1 |
| 5,607,417 A | 3/1997 | Batich et al. | 604/890.1 |
| 5,641,562 A | 6/1997 | Larson et al. | 442/394 |
| 5,643,241 A | 7/1997 | Ahr et al. | 604/385.1 |
| 5,649,914 A | 7/1997 | Glaug et al. | 604/361 |
| 5,653,862 A | 8/1997 | Parris | 205/777.5 |
| 5,658,268 A | 8/1997 | Johns et al. | 604/361 |
| 5,678,564 A | 10/1997 | Lawrence et al. | 128/761 |
| 5,681,298 A | 10/1997 | Brunner et al. | 604/361 |
| 5,702,376 A * | 12/1997 | Glauge et al. | 604/361 |
| 5,728,125 A | 3/1998 | Salinas | 604/361 |
| 5,733,272 A | 3/1998 | Brunner et al. | 604/359 |
| 5,736,590 A | 4/1998 | Rasmussen | 523/113 |
| 5,760,694 A | 6/1998 | Nissim et al. | 340/604 |
| 5,769,834 A | 6/1998 | Reiter et al. | 604/385.1 |
| 5,797,892 A | 8/1998 | Glaug et al. | 604/361 |
| 5,876,393 A | 3/1999 | Ahr et al. | 604/387 |
| 5,947,943 A * | 9/1999 | Lee | 604/361 |
| 6,093,869 A * | 7/2000 | Roe et al. | 604/361 |
| 6,147,037 A * | 11/2000 | Gardlik et al. | 510/107 |

\* cited by examiner

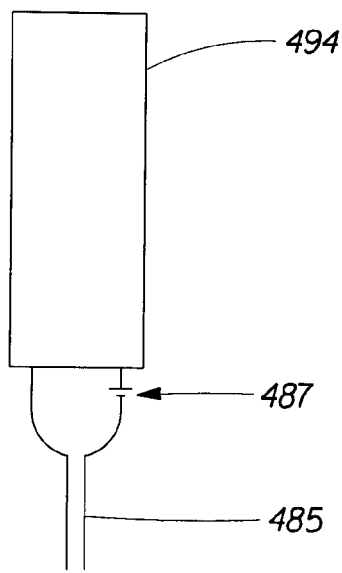
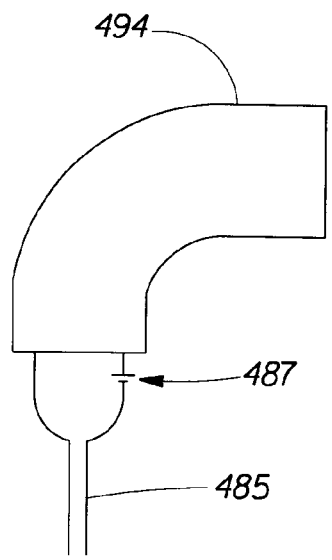
Fig. 10A
Fig. 10B
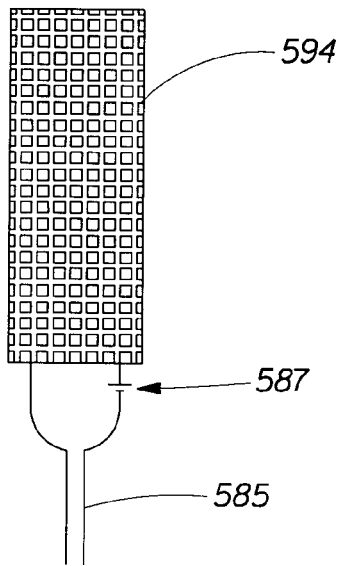
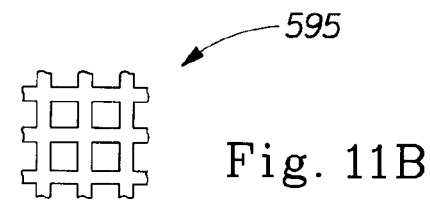
Fig. 11B
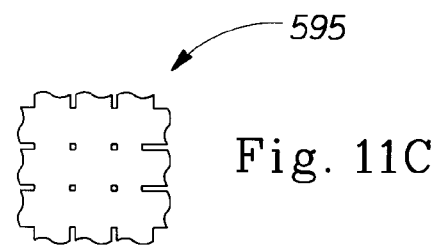
Fig. 11C
Fig. 11A

DISPOSABLE TREATMENT ARTICLE HAVING A RESPONSIVE SYSTEM

This is a continuation-in-part of Ser. No. 09/107,561, filed Jun. 29, 1998 and Ser. No. 09/106,225 filed Jun. 29, 1998 and claims benefit of provisional application Ser. No. 60/090,993 filed Jun. 29, 1998.

FIELD OF THE INVENTION

The present invention relates to disposable articles and, more particularly, to disposable treatment articles having a responsive system that acts continuously or discontinuously.

BACKGROUND OF THE INVENTION

Today, disposable articles are widely used for treatment of living and non-living surfaces for a wide variety of purposes. For example and without limitation, disposable products are used in the areas of personal care items, pharmaceuticals and health care, baby care, textile care, and home, commercial and industrial cleaning. These disposable products may be used for purposes such as, but not limited to cleaning, applying coatings or other materials to treat surface (such as stains, paints, waxes, conditioning agents, etc.), and containing or removing materials such as wastes, contaminants or other excess or undesired materials (such as diapers for body wastes, mops, brooms, gloves, etc. In many cases these articles have replaced reusable articles as the preferred means for reasons such as cost, convenience, and sanitation.

While many advancements have been made in the field of disposable articles to improve their effectiveness, such as improved strength, addition of active ingredients to improve cleaning, use of absorbent gellants to improve absorptivity, etc., a number of problems still exist. Among the problems experienced with these disposable treatment articles are leakage of materials intended to be removed or isolated, which can lead to incomplete cleaning and contamination of the surface that was treated by the material that was intended to be removed or isolated by the article, etc.

Another problem is that disposable treatment articles to date do not discriminated between when a particular type of treatment is needed and when it is not. For example, a disposable wipe may be used for general cleaning as well as to biological contaminants (such as wiping away feces from surface of a baby's skin). Wipes designed to remove feces from a baby's buttocks contain disinfectants or other active ingredients that may not be needed, or undesired, for other uses, such as wiping food from the baby's face, or wiping stains from a textile surface or floor. Further, in the event that the disposable article is to be used multiple times before disposal, an active ingredient needed for treating a particular condition, such as disinfection of the skin in association with removal of feces, may no longer be present or effective for its intended purpose.

SUMMARY OF THE INVENTION

The present invention is directed to a disposable treatment article having a responsive system that acts in response to an input such as a material, condition, or occurrence to provide a responsive function which treats a material or object that can be either directly or indirectly associated with the input.

The present invention provides, for example, a self-contained, disposable treatment article, comprising a responsive system including;

(i) a sensor operatively connected to said article, said sensor being adapted to detect an input, and (ii) an actuator operatively connected to said sensor, said actuator being adapted to perform a responsive function upon said input, said actuator comprising a distinct component from said sensor, and (iii) optionally, a feedback control loop in which said controller is adapted to allow said actuator to perform said responsive function upon said input when said sensor detects said input.

The responsive system is preferably operatively connected to the article or can constitute the entire article. Preferably the article further comprises a disposable substrate, preferably a planar substrate, and optionally comprises further structural elements which may be disposable or non-disposable. The responsive system may be attached to, or disposed on or in the substrate or further structural elements. Preferably the responsive system is disposable and if all or part is connected to a non-disposable element, it is releasably connected so that it can be removed and replaced.

While the specification concludes with claims that particularly point out and distinctly claim the present invention, the following description taken in conjunction with the accompanying drawings describe the invention and preferred embodiments thereof.

BRIEF DESCRIPTION OF THE DRAWINGS

FIGS. 10A and 10B show an embodiment of a responsive system of the present invention including an electrically sensitive gel.

FIGS. 11A, 11B and 11C show another embodiment of a responsive system of the present invention including an electrically sensitive gel.

FIG. 13A is a perspective top view. FIG. 13B is a bottom plan view of the mop head.

FIG. 14A is a perspective top view. FIG. 14B is a plan view of the mop head cover. FIG. 14C is a perspective top view of FIG. A wherein the mop head cover is positioned in place on the mop head.

DETAILED DESCRIPTION OF THE INVENTION

Figure 1A:
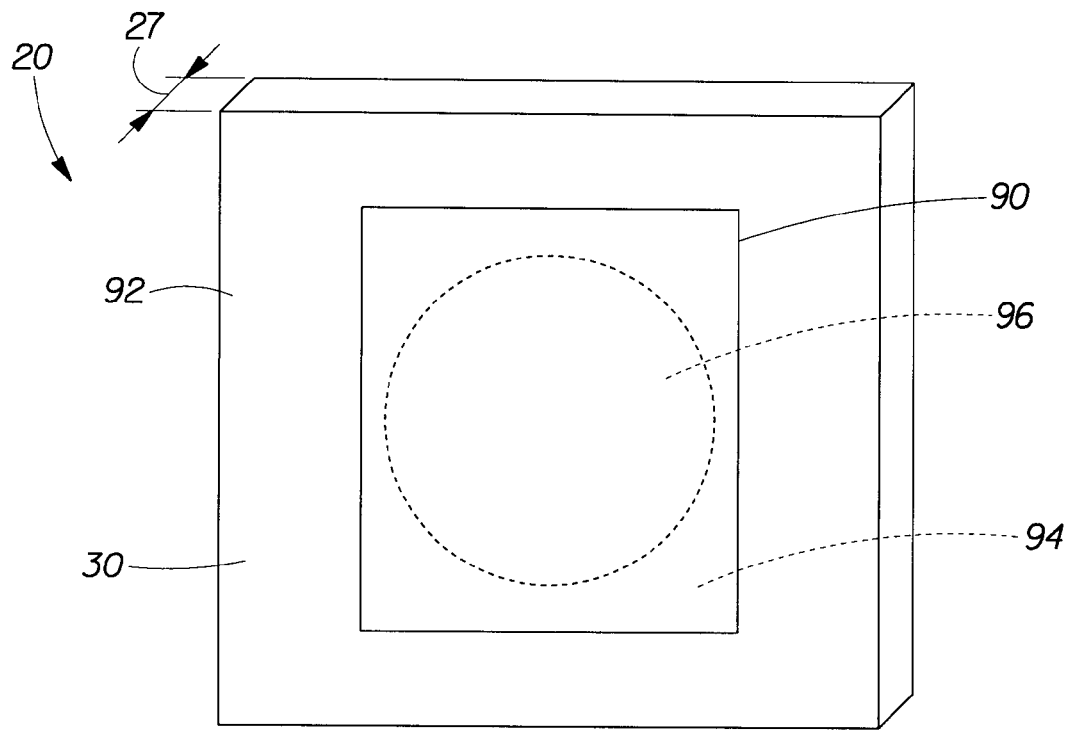
FIG. 1A is a perspective view of the article made in accordance with the present invention wherein the article is a planar substrate, such as a tissue, paper towel, or wipe.

As used herein, the term "disposable" is used herein to describe articles which generally are not intended to be laundered, recharged, refilled, or otherwise restored or reused as an absorbent article (i.e., they are intended to be discarded after a single use or a few uses (generally three or less) and, preferably, the components, parts, or materials of the article to be recycled, composted or otherwise disposed of in an environmentally compatible manner). A disposable article hereof may be an article that is intended to be disposed of in its entirety after its useful life or an article having a combination of reusable parts and disposable parts which form a unitary article, wherein only the disposable part(s) is(are) disposed of after its(their) useful life.

As used herein, the term "disposed" is used to mean that an element(s) of the article is formed (joined and positioned) in a particular place or position as a unitary structure with other elements of the article or as a separate element joined to another element of the article. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. A "unitary" article refers to articles which are formed of separate parts united together to form a coordinated entity so that they do not require separate manipulative parts during use.

The term "absorbent article" refers to devices which absorb and contain liquid (including gaseous) or semi-liquid substances. Absorbent articles include without limitation water absorbing, oil absorbing, alcohol absorbing, or other fluid-absorbing articles.

As used herein "treat" means to move, remove, isolate, modify, or otherwise affect an object. An object intended to be treated can be inanimate or animate, and includes without limitation any material, device, person, animal, ambient environment or atmosphere, or a component thereof. To treat an object can include, without limitation, removing, isolating, or modifying a material located on the surface or within the material or object. "Treatment" refers to the act of treating. A "treatment article" means an article capable of treating an object. Treatments can by way of example and without limitation encompass: cleaning; delivering a substance; removing a material (such as without limitation a contamination or irritant); isolating a material such as by containing it in a compartment, void, or absorbent material, or by coating it; and modifying a material by changing its biological, activity, chemical identity, structure, properties, pH, or form, physical state, physical form, or chemical, electrical, or optical properties; and combinations thereof. Modification of a material or object can be achieved, without limitation, by delivering a substance (e.g., an active ingredient) to the object or by application of energy, or a combination thereof.

As used herein, "self-contained" in the context of a self-contained treatment article means the article comprises both sensor and actuator wherein the actuator includes suitable structure, materials, treatment agents, and/or energy to carry out a responsive function as part of a unitary structure of the article.

The articles hereof can be used in any field of use including without limitation, personal care, health care, baby care, home and household care, cleaning products, disinfecting and./or sanitizing products, textile treatment, personal care, cosmetics, medical care and pharmaceuticals, etc. The above examples are, indeed, intended only as examples and it will be apparent that numerous of the articles may be categorized under more than one of the categories of articles, for example a mop may be both a cleaning article and an absorbent article.

Sensor

The disposable articles of the present invention comprise a sensor operatively connected to the article. As used in this application, the term "sensor" refers to a device that is capable of detecting an input. An input is an event or a parameter that is associated with an event. A parameter associated with an event is any measurable signal that correlates with the occurrence of an event within the frame of reference of the system. Sensors include anything that responds to one or more specific inputs, including electrical, chemical, biological, biochemical, physical, or mechanical properties. Examples of inputs that may be detected by the sensor of the present invention include, but are not limited to, attitude, pressure, flow rates, motion, moisture, enzymes, bacteria, pH, conductivity, resistance, capacitance, inductance, electrical and/or electromagnetic fields, light, presence of a material or substance or change in the condition of a material or substance, other properties or events (e.g., occurrence or presence of a material) and combinations thereof. Mere passage of time, without other input, does not constitute an input for purposes of the present invention. An electrical or biological sensor may, for example, detect presence of a material (such as but not limited to a pathogen, a fluid, a bodily waste) by sensing a component of the material. A sensor may detect one or more events or one or more parameters associated with an event and provide an input to an actuator or a controller. Further, a sensor of the present invention may also be reversible or irreversible. A dissolving film or capsule is an example of an irreversible sensor, while an electrical sensor that detects electrical activity or static charge of or on an object may receive multiple sequential input signals (i.e., is reversible).

A chemical sensor or biosensor may respond to chemical and/or biochemical inputs such as but not limited to enzymes or other components typically present in contaminants, body fluids and wastes such as blood, urine, feces, and saliva, pH, water, or other biological inputs such as bacteria, viruses, biological degradation products (such as those derived from breakdown or degradation of bacteria, or other biological organisms or materials). A chemical sensor may use a chemical reaction as a detection means or may involve a dissolution of a material soluble in an input material of interest. Examples of chemical or biological sensors include dissolving or rupturable films, capsules, cells, seals, etc. that dissolve or rupture in response to a specific chemical, biochemical or biological input or to a specific class of chemical, biochemical or biological inputs. A mechanical sensor may also respond to motion, attitude, pressure, etc. An example of a mechanical sensor is a bellows-type in which when an object is placed on the sensor the weight pushes down on the bellows to inflate a portion of the sensor. A mechanical sensor may also include a sensor or a portion of the sensor that is broken or separated under a pre-defined applied pressure. An electrical sensor may also be used to respond to an input such as but not limited to moisture, urine, blood, feces, menses, pressure, resistance, capacitance, inductance, static charge, etc. An electrical sensor may, for example, include a sensor in which a conductive input (such as one containing water) completes an electrical circuit; a sensor in which an input such as pressure or tension closes an electrical contact to complete a circuit; a piezoelectric sensor that generates a signal via pressure induced during use or by a user or wearer (e.g., from motion or muscle tone); a sensor in which the resistance, capacitance or inductance varies in the presence of the input to which the sensor responds; or a sensor that receives electrical signals from the body (e.g., from the subcutaneous muscles) of the wearer or user through a contact such as a skin contact sensor. A thermal sensor may also be used to detect changes in temperature. Optionally, the sensor may be a biosensor as known in the art (e.g., an enzyme sensor, organella sensor, tissue sensor, microorganism sensor, or electrochemical sensor). The sensor may be adapted to detect proteins, sugars, bile components, etc. such as described in U.S. Pat. No. 4,636,474 entitled "Toilet Apparatus," issued to Kenji Ogura et al. on Jan. 13, 1987. Biosensors may comprise bio-recognition systems, typically enzymes or binding proteins such as antibodies immobilized onto the surface of physico-chemical transducers. The biosensors may detect components of bodily wastes, such as ammonia and phenol (e.g., via biosensors comprising enzyme electrodes). A specific strain of bacteria may be detected via biosensors employing antibodies raised against that bacterial strain. Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively.

Optionally, the sensor may be a "proactive sensor" that is capable of detecting changes or signals relating to the event that is measured. For example this can include changes in or to an object to be treated, such as the body of the wearer or surface to be treated, in the article, or in the waste or contaminants that directly relate or, at a minimum, correlate to the occurrence of an impending event. A proactive sensor, for example, may detect an impending event such as a defecation, urination or discharge, medical condition, infestation of insects or parasites, etc. or a parameter that correlates to an event. The impending event may be related to the bodily waste, the wearer or user, the article, or a component or components thereof A parameter that correlates to an event is any measurable input signal that correlates with the occurrence of the event within the frame of reference of the system (i.e., a signal caused by the user or the wearer). The proactive sensor may, for example, predict the occurrence of an event or may detect signals that may precede an event, such as predicting the onset of a medical condition (e.g., illness, skin rash, acne) by detecting presence of bacteria or skin irritants that precede onset of the condition, respectively). The proactive sensor may also predict environmental effects such as insect infestation by detecting insect eggs or spores, or mold and fungus by detecting spores. Proactive sensors in an article may measure many different inputs in order to predict an event For example the sensor may detect residual fecal contamination (e.g., fecal enzyme residue left after cleaning up a floor soiled by dog that has not been house-trained, or a baby's skin in the vicinity of the buttocks) that may lead to malodor, spread of bacterial infection, or irritated skin. Detection of a high pH, an increased skin hydration resulting in a measurable increase in conductance or decrease in impedance of skin, etc. may also be used to predict potential skin irritation. Further embodiments of a proactive sensor are described in copending U.S. application Ser. No. 09/107,561 entitled "Disposable Article Having A Proactive Sensor" filed on Jun. 29, 1998, which is herein incorporated by reference.

The sensor may be disposed in and/or operatively connected to any portion of a disposable article that will be exposed to the input, that the sensor is designed to detect. For the purposes of the present invention, the term "operatively connected" refers to a means of communication such that the sensor may signal some portion of the article when the sensor detects an input. The sensor may be separate from and operatively connected to another portion of the sensor another sensor an actuator a controller or some other portion or component of the article. "Operatively connected" may, for example, include a means of communication such as an electrical connection via a conductive wire or member, via a transmitted signal such as radio frequency, infrared or another transmitted frequency communication. Alternatively, the sensor may be operatively connected via a mechanical connection such as a pneumatic or a hydraulic connection.

The sensor may further comprise a sensing "system" including two or more sensors, each of which may detect the same or different signals from the same or different sources. For example, the sensing system may include a sensor inside the article that detects electrical or biological signals from one or more external and/or separate sensors, such that when specified types of signals are sent or specified combinations of signals are sent, the sensor inside the article the actuator performs a responsive function. For example, when a biological input is detected in a certain type of fluid and also having a having a certain pH the article may release an anti-microbial selected to be effective under those particular conditions. The sensing system may include components that are located inside, external to and/or separate from the article.

Actuator

The article of the present invention also comprises an actuator. As used in this application, the term "actuator" refers to a device that comprises "potential" and a means of transforming that potential to perform or activate a "responsive function." The potential of the actuator may comprise either stored or potential energy or stored material. The actuator thus may perform or activate a responsive function by transforming potential energy to kinetic energy or by releasing or delivering a stored material. Potential energy may be stored as mechanical, electrical, chemical or thermal energy. "Kinetic energy" as used in this application refers to the capacity to do work or to perform a responsive function as described above (e.g., expansion of a compressed device, rotation of a twisted device, a gel that moves as it changes phases, coating or treatment of a material or object.

A "responsive function" is defined for the purposes of this application as a function performed upon the object to be treated. The object to be treated can be a substance or material, the article itself, a wearer or user of the article, an animate organism, a device, or a component thereof For the purposes of the present invention, a function is considered to be performed upon the input if the function is performed upon the element sensed or upon another element directly or indirectly associated with the element sensed.

In the typical embodiments of the invention, the actuator will treat an object by performing one or more of the following responsive functions: deliver a material to treat an object; deliver electrical (defined herein to include electromagnetic energy) to treat an object; deliver mechanical energy to treat an object. Delivering energy in accordance with the above categories can include, in addition to what may be disclosed below, moving a material, removing a material, isolating a material. Isolating an object as will be discussed further below can also include delivering a material to an object in order to isolate the object.

The treatment performed by the present invention can be directed toward a wide variety of user-beneficial outcomes including, but not limited to: cleaning, bleaching, staining, coloring, sanitizing, polishing, deodorizing, disinfecting, medicating, drugging, chemically etching, surface modifying, smoothing, dyeing, de-gumming, coating, encapsulating, picking up materials, chemically reacting, sealing, lightening, darkening, frosting, greasing, thickening, gelling, painting, inking, printing, scenting, saturating, drying, absorbing, adsorbing, detoxifying, de-static"fying", de-magnifying, magnifying, tackifying, de-linting, plating, purifying, basting, wiping, chemically reacting including oxidizing, reducing and neutralizing, solidifying, liquefying, hardening, softening, tanning, treating, moisturizing, lotioning, salting, thinning, styling, preserving, lubricating, cleansing, and dissolving.

Exemplary treatment functions for the actuator include delivering a material such as an active ingredient to clean, condition, color, modify, chemically react with, catalyze a chemical reaction with, sanitize, disinfect, sterilize, kill (such as insects, microorganisms), coat, modify pH, modify biological activity, inhibit, or protect an object. Exemplary, non-limiting specific examples include treating a material or object such as: hard or soft surface such as glass, floors, skin, plates, utensils, tables, metal, wood, plastics, ceramics; textiles such as clothes, carpets, upholstery; modifying the physical nature of a material by adding a chemical composition that modifies the physical properties of it such as by modifying viscosity, surface energy, or other physical properties, or facilitating or causing a chemical reaction with the material.

Exemplary treatment functions for delivering electrical or electromagnetic energy include plasma surface treatment, magnetization and demagnetization, creating static charge and eliminating a static charge (e.g., via electrostatic spray to charge or neutralize a surface charge).

Exemplary treatment functions for delivering mechanical energy to treat a material or object include physically manipulating the material or object such as by massaging, mixing, abrading, spreading, or loosening their adhesion to a surface.

Exemplary treatment functions for removing or isolating an object include removing or isolating body fluids or defecation, contaminants, spoiled foods, biodegraded materials such as foods, biodegradable plastics, oils, etc.

An actuator of a disposable article may, for example release or deliver a deodorant, enzyme inhibitor, anti-microbial, anti-fungal, skin care composition, cleaning agent, surface modification agent, or pH control agent; capture, wipe, cover, trap, immobilize, seal, pump, or store bodily fluids, bodily waste, contaminants, dirt, dust, garbage, or any other substances whose presence is undesired; or trigger the release or creation of a structure or element designed to perform one or more of these functions or any other responsive function upon the waste, wearer, article, or a component thereof An actuator of a disposable article, for example and as discussed above, may deliver a material to an object. In order to do so it may deliver to an object one or more active ingredients such as but not limited to those selected from the group consisting of antimicrobials, antifungals, enzyme inhibitors, pH buffers, pH modifiers, cleaning agents, conditioning agents, drugs, absorbent materials, cosmetics, protective agents (e.g., waxes, barrier creams. for skin, hard surfaces, etc.), powders, anti-adherents (e.g., silicones), and rheology modifiers. Preferably the delivered materials are stored in the article. Materials and active ingredients that can be delivered include but are not limited to one or more of the following: conditioning agents, cleaning agents (e.g., surfactants, preferably anionic and nonionic surfactants), disinfectants, antifungals, anti-microbials, chemical reactants, drugs, biologically or physiologically active agents (e.g., enzyme inhibitors), rheology modifiers (e.g., feces modification agents), pH buffers or modifiers, dyes; pressurized gas, a compressed foam, a twisted foam, a pump, a closed system liquid transport member, an electrically sensitive gel, a pH sensitive gel, a salt concentration gel, etc. Rheology modifiers include but are not limited to feces modifying agents, thickeners (e.g., polymeric thickeners, clay, etc.), suspending agents, and viscosity reducers. Conditioning agents can be used to condition animate or inanimate objects including but not limited to textiles, hair, fibers, skin, and leather. Examples include cationic surfactants, cationic polymers, oils, waxes, shine agents, silicones, hydrocarbons, emollients, moisturizers, etc.

Isolating an object can be accomplished by coating it, capturing it in a void, container, or other three dimensional structure, or moving it to another location (which may involve removing it from its proximate location or merely adjusting its position while remaining proximate to its original position.

A device that merely provides a signal indicating that an event has occurred, however, is not considered an "actuator" as defined for the purposes of this application.

Triggering the creation of a three dimensional structure to remove a material from a location (such as a surface) or to otherwise isolate an object can involve responsive functions performed on a component of the article and, ultimately, on the material. Capturing a substance to be removed, wiping a surface of the object to be treated or the skin of the user or wearer, or treating the surface of an object or the skin of a user or wearer with a composition that cleans or modifies the surface or skin, or component thereof, or a material or substance on such skin or surface, for example, are responsive functions performed on the contaminant and/or the surface or the user or wearer. Adjusting the article's geometry (in one, two or three dimensions) or physical properties (e.g., bending modulus, geometry, etc.) are examples of responsive functions, which may be performed by the article.

Signaling a caretaker and/or the wearer that an event has occurred, however, does not perform a responsive function because it does not perform a function upon an object or material. Signaling devices require an agent external to the system (e.g., a human, etc.) to act as an actuator to result in a function being performed.

An actuator of the present invention may release potential energy to perform or activate a responsive function upon the object to be treated. The object to be treated can be inanimate or animate, including for example without limitation a material, device, surface, person, animal, or environment (e.g., ambient air). The release of potential energy may transform mechanical, electrical, chemical or thermal potential energy into mechanical, electrical or chemical kinetic energy to perform the responsive function. Actuators may be triggered by a threshold level of an input to release potential energy to perform a responsive function or may respond continuously to an input as described below. For example, a compressed foam has stored compressive mechanical potential energy and may provide mechanical kinetic energy when it is released. A twiste[0084] foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy.

Potential energy may be stored in any manner sufficient to maintain/restrain it until it is required. Examples include batteries and/or capacitors, elastically, torsionally, compressively tensioned materials or structures, in the form of unreacted reagents, and materials capable of performing physical or chemical functions (e.g., absorbents, emollients, pH buffers, enzyme inhibitors, feces modification agents; compressed gases, etc.).

Alternatively, an actuator of the present invention may comprise a quantity of a stored material that has the capacity to perform or activate a responsive function upon the object to be treated. In one embodiment, for example, the actuator may release or deliver a stored material that performs a responsive function. In this embodiment, the actuator may be triggered by a threshold level of an input to discontinuously release or deliver the stored material at a given time or may release or deliver the material continuously.

In alternative embodiments the sensor and/or actuator may comprise a closed system liquid transport member. A "closed system liquid transport member" or "transport member" comprises a liquid filled member having an inlet port and outlet port, which upon receipt of liquid at the inlet port releases liquid at the outlet port. The liquid released from the outlet port may serve as an input signal to a sensor. For example, the liquid may be water, which is released when the transport member imbibes urine at an inlet port, which acts to dissolve a seal to release stored mechanical energy to deliver a material or create a void space to isolate a material. Alternatively, the transport member may itself trigger an actuator (e.g., mix with agents to perform a chemical reaction), or may perform at least a portion of the actuator function (e.g., the released water is imbibed by a super absorbent polymer arranged in a particular geometry, which swells and forms a feces void volume). Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member must have a relatively high liquid permeability.

There are preferably at least two regions within the transport member with different pore sizes, namely the one or more port region(s) having smaller pores and the inner region having a much larger pore size. The inner region of the transport member has a permeability that is relatively high compared to the permeability of a port region (a higher liquid permeability provides less flow resistance), which can be a part of an outer/wall region circumscribing the inner/bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108,383 entitled "Membranes for Absorbent Articles" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Rüschlikon, Switzerland.

The actuator may alternatively comprise an electrically sensitive gel. Electrically sensitive gels are polymeric gel networks that, when at least partially swollen with water, change volume and/or geometry under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometry's such as rectangular, circular, reticulated grid, etc. patterns in order to provide a valve to release a material, allow a fluid to flow through, prevent a fluid from flowing through, encapsulate a fluid or other substance (e.g., bodily waste), etc. as they change volume and/or geometry. An electrically sensitive gel formed in a strip, for example, may be bent to transport feces when fecal moisture is detected. In FIGS. 10A and 10B, for example, a strip of electrically sensitive gel is shown in a circuit in which fecal moisture may bridge the contacts 485 and allow current to flow to the electrically sensitive gel either bending or straightening the strip. Alternatively, an electrically sensitive gel formed in a reticulated grid pattern, such as shown in FIGS. 11A, 11B and 11C, may be electrically induced to swell or shrink when electrically conductive fluid is detected to form a valve that allows and/or prevents urine flow to another portion of the article 20. FIG. 11A, for example, shows a circuit including a reticulated grid pattern of an electrically sensitive gel. FIGS. 11B and 11C further show a microscopic view of the grid in a shrunk and in a swelled configuration, respectively. An exemplary material is a weakly cross-linked PAMPs gel (poly(acrylamido-2-methyl propane) sulphonic acid). This type of gel may perform various functions such as the creation of a void space for an object to be removed or isolated from a surface (e.g. feces), wiping the skin or other surface, applying or delivering a chemical agent, or functioning as a valve to release a material. Other exemplary electrically sensitive gels are described in U.S. Pat. No. 5,100,933 issued to Tanaka on Mar. 31, 1990 and WO 9202005. Alternatively, pH sensitive gels, salt concentration sensitive gels that change volume and/or geometry at specific pH or salt concentrations, respectively, or gels that are sensitive to other properties materials, or conditions may be used as an actuator of the present invention.

An embodiment of an article of the present invention may include one or more proactive sensors and one or more actuators. By detecting an input signal prior to the impending event, a responsive system in the article may be triggered to prepare for the impending event. This will allow the construction of articles in which the treatment technology is initially "hidden" or unobtrusive, but which is available at, or just before, the moment of need. Regardless of the specific input, the proactive sensor in these embodiments may trigger an actuator to perform an action on the object to be treated to prepare for the occurrence of the event. For example, if an impending biological event (e.g., illness, skin irritation, insect infestation, etc.) is to be detected the system is preferably triggered (i.e., the responsive system is activated) by a biological signal related to the presence of event that is predictive of the impending event to be treated or prevented.

The actuator 70 may be disposed in and/or operatively connected to any portion of the disposable article that will allow the actuator to perform a responsive function. The actuator 70 may also be completely contained within the article such as article 20, may have a portion located in the article and a portion located outside the article 20, or may be completely external to the article 20. An actuator 70 or a portion of an actuator 70 may be operatively connected to one or more sensors 60, one or more controllers 80, another portion of the actuator 70 or another portion of the article 20. Further, the actuator 70 may be integral with the article 20, or may be installed by the user.

The article may also include a controller. A "controller" is defined for the purposes of this application as a device that receives an input from a sensor and determines if one or more actions are to be taken. A controller 80 may receive a signal from the sensor 60 and direct the actuator 70 to perform a responsive function upon the bodily waste, the wearer, the article or a component thereof Alternatively, the actuator 70 may receive the signal directly from the sensor 60 and perform a responsive function upon the wearer, the waste, the article or a component thereof A controller may include materials that undergo chemical or physical change, may be a chemical, mechanical or electrical device that processes information from a sensor, etc. For example, in an article having a compressed plastic foam material encapsulated and restrained under vacuum by a moisture soluble bag, the sensor 60 may comprise the moisture soluble bag. The physical and chemical characteristics of the film, i.e., the type of polymer, the thickness, etc., that determine how much of the input must be present before the film will dissolve act as the controller 80 and determine the threshold level of input that must be met before the controller 80 allows the actuator 70 to release stored energy to perform a responsive function. The actuator 70 is the combination of the compressed foam and the loss of vacuum, which allows release of the stored mechanical energy of the compressed foam. In this example, the controller 80 acts as a one-time switch. An electrical controller 80 that receives signals from the sensor 60 such as electrical activity of muscles of the wearer, however, may receive and monitor multiple electrical signals and may repeatedly trigger the actuator. The controller may be integral with the sensor component, integral with the actuator component, or a separate component of the system.

The controller 80 may be disposed in and/or operatively connected to any portion of a disposable article that will allow the controller 80 to receive a signal from the sensor 60 and to provide a signal to the actuator 70. The controller 80 may be integral with the article 20, or may be installed by the user. The controller 80 may be completely contained within the article such as article 20, may have a portion located in the article and a portion located outside the article, or may be located completely outside the article 20. A controller 80 or a portion of a controller 80 may be operatively connected to one or more sensors 60, one or more actuators 70, another portion of the controller 80 or another portion of the article 20. The controller 80, for example, may receive a signal from the sensor 60 and provide a signal to the actuator 70, e.g., by a radio frequency (rf) transmission.

Although distinct structural elements may perform the sensor 60, actuator 70 and controller 80 functions, the sensor 60, actuator 70 and/or controller 80 functions of the present invention need not be performed by distinct structural elements. The sensor 60 and controller 80 functions, for example, may be performed by the same structural element such as a film that dissolves in contact with a component of a material to be treated, e.g. waste. In this example, the film acts as a sensor and responds to the input. The physical and chemical characteristics of the film, i.e., the type of polymer, the thickness, etc., that determine how much of the input must be present before the film will dissolve act as the controller and determine the threshold level of input that must be met before the controller allows the actuator to release stored energy to perform a responsive function. In another embodiment, the responsive system may comprise cells or capsules that contain one or more materials for treating the intended object. The cells or capsules may, for example, burst under a threshold pressure level or dissolve in the presence of a threshold level of a given liquid or other component of bodily waste or other contaminant and release a stored treatment material (e.g., a skin care composition or enzyme inhibitor). In this embodiment, the cells or the capsules act as both the sensor, e.g., detecting the pressure level, and the controller, e.g., defining the threshold pressure level before allowing the stored treatment material to be released. In yet another embodiment, the responsive system may comprise a closed system liquid transport member. In this embodiment, the transport member both acts as the sensor and the actuator, i.e., actively delivering the treatment material from the outlet port to the object to be treated. In addition, the closed system liquid transport member may further act as a controller that determines the necessary threshold level of the input. In an embodiment in which the closed system liquid transport member receives a fluid to be treated at the inlet port and liquid such as water exits from the outlet port to dissolve a soluble film holding a compressed resilient material, for example, the closed system liquid transport member may act as both the sensor and the controller. In this embodiment, the transport member acts as a sensor by receiving the fluid to be treated (e.g., urine) and the permeability of the inlet port or the outlet port may function as the controller and determine the threshold quantity of liquid that is required before the transport member delivers liquid to the soluble film.

The article 20 of the present invention preferably includes a discontinuous responsive system with or without a feedback control loop. The responsive system may alternatively include a continuous responsive system having a feedback control loop. For example, an absorbent article may comprise a responsive system that acts upon the contaminant, e.g., bodily fluid, when the contaminant body waste is sensed by the sensor. A "responsive system" is defined for the purposes of this application as a system that includes a sensor 60 and an actuator 70 that acts upon the object to be treated when the sensor 60 detects the appropriate triggering input. Upon sensing a given input parameter, the actuator 70 effects the release of stored energy or material to perform a responsive function.

The responsive system of the present invention may respond in either a "continuous" or a "discontinuous" manner. As used in this application, a "continuous responsive system" refers to a responsive system in which the output is quantitatively dependent upon the quantity of the input, i.e., continuously increasing quantities of the input are required to effect continuously increasing quantities of the output, or where the output of the responsive system comprises a passive release of a stored material. A super absorbent polymer placed in an absorbent disposable article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+excess B→C, for example, the amount of excess B converted to C is stoichiometrically and, therefore "continuously," related to the amount of A available in the system. A responsive system that passively releases a stored material, however, generally provides a continuous response regardless of how the material itself is released because the actual responsive function performed upon the object to be treated is performed by the material,: not by the release of the material. Thus, whether the material is released continuously in response to a given input, or released discontinuously at a single time when a threshold of a given input is detected, the responsive function performed by the released material is performed such that continuously increasing quantities of the input are required to effect continuously increasing quantities of the output until the material released is exhausted.

Figure 7A:
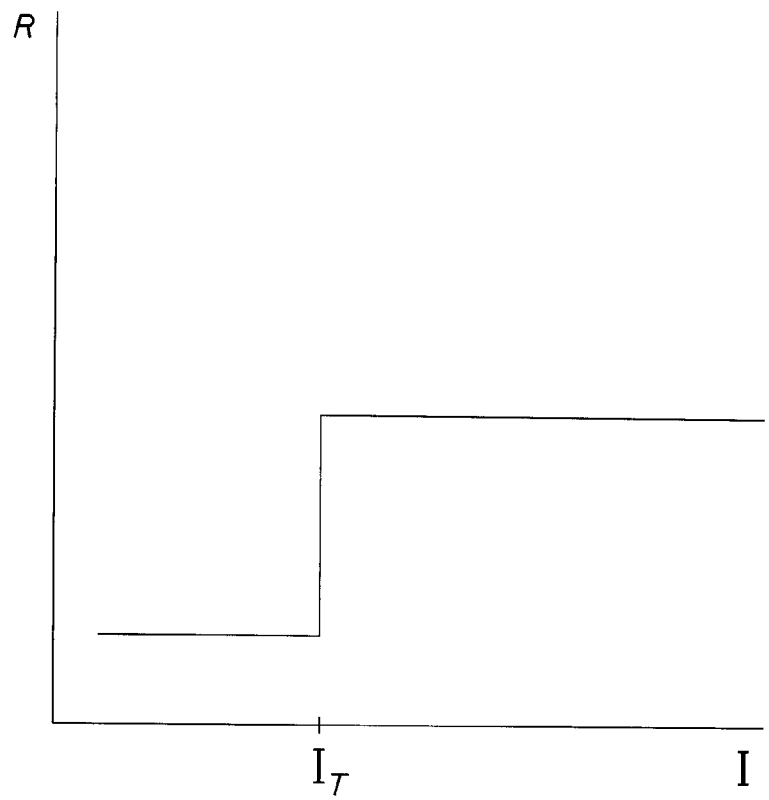
FIG. 7A shows an ideal output function of a discontinuous responsive system of the present invention having a single threshold level.

A "discontinuous responsive system," however, refers to a responsive system that has an output function that is essentially independent of the quantity of the input beyond a threshold level. For example, when one or more threshold levels of a given input are met, the responsive system may release all or a pre-designated portion of its stored energy to perform a specific responsive function. In an ideal embodiment of the present invention, the output function includes a "step" function as shown in FIG. 7A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function $f(x-\epsilon)$ as $\epsilon \to 0$ is not equal to the limit of the function $f(x+\epsilon)$ as $\epsilon \to 0$, i.e., $\lim_{\epsilon \to 0} f(x-\epsilon) \neq \lim_{\epsilon \to 0} f(x+\epsilon)$.

Figure 8A:
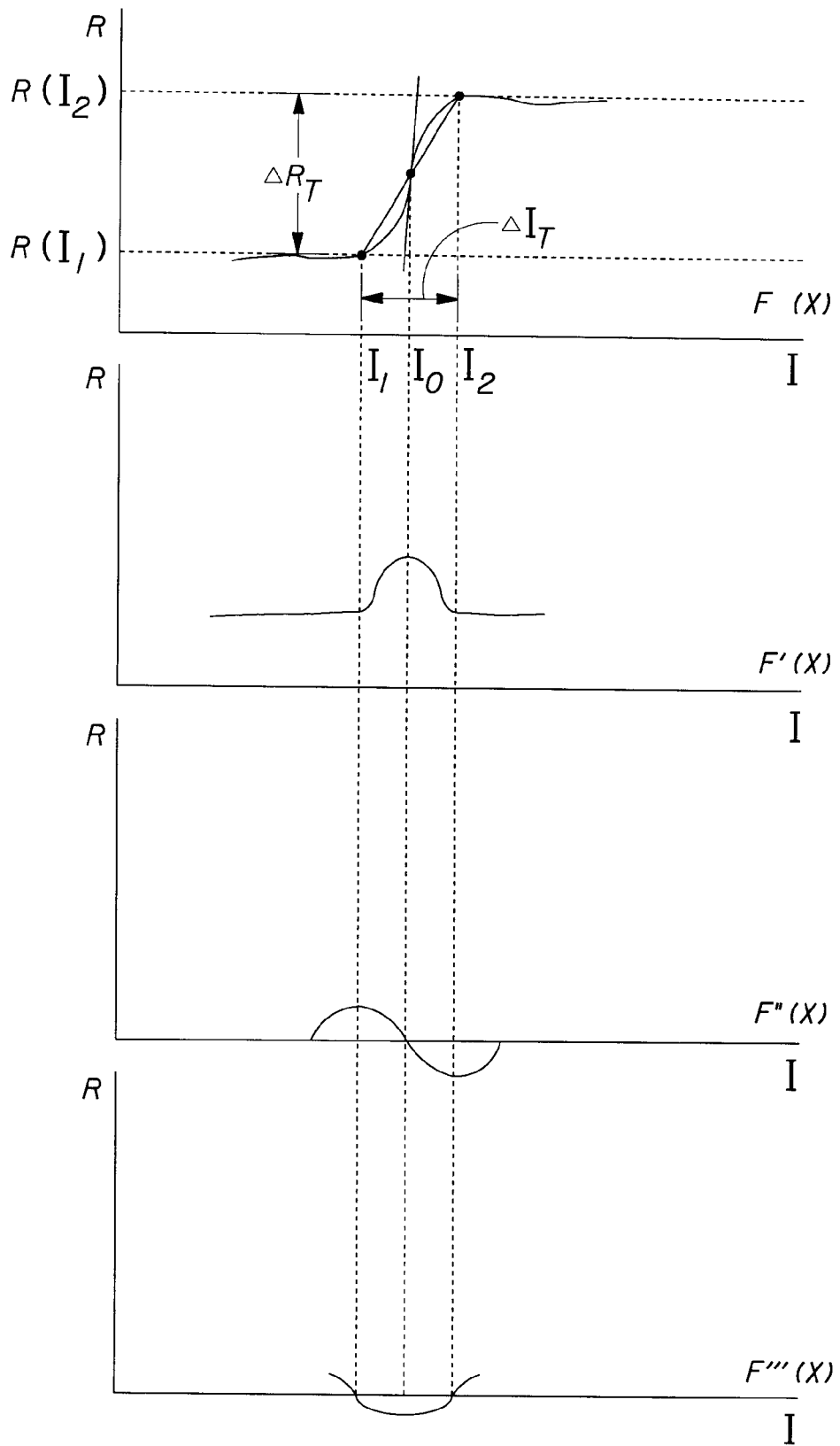
FIG. 8A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 8A shows a graph of an exemplary output function, f(x) along with aligned graphs of the first, f'(x), and second, f"(x), and third, f'''(x), derivatives of the exemplary output function. The output function f(x) describes the effect of the input (x or I) on the output or response (R(I)). For purposes of the present invention, the transition region is defined as the region between the relative maxima, $R(I_1)$, and the minima, $R(I_2)$, of the second derivative, f"(x), of the output function, f(x). The relative maxima, $R(I_1)$, and the relative minima, $R(I_2)$, are points at which the third derivative, f'''(x), equals zero. The inflection point, $I_0$, is defined as the point in the transition region at which the second derivative, f"(x), equals zero, i.e., $$\left. \frac{d^2 R}{dI^2} \right|_{I=I_0} = 0.$$

The comparison of the slope of the output function at the inflection point to the slope of a line between the first and the last points of the transition region can be described by the equation:

$$\left.\frac{dR}{dI}\right|_{I=I_0} = k\frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2-I_1$, and the term $\Delta R_T$ is the change in the response of the output function between the first and last points of the transition region, i.e., $R(I_2)-R(I_1)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100 being the most preferred.

Figure 8B:
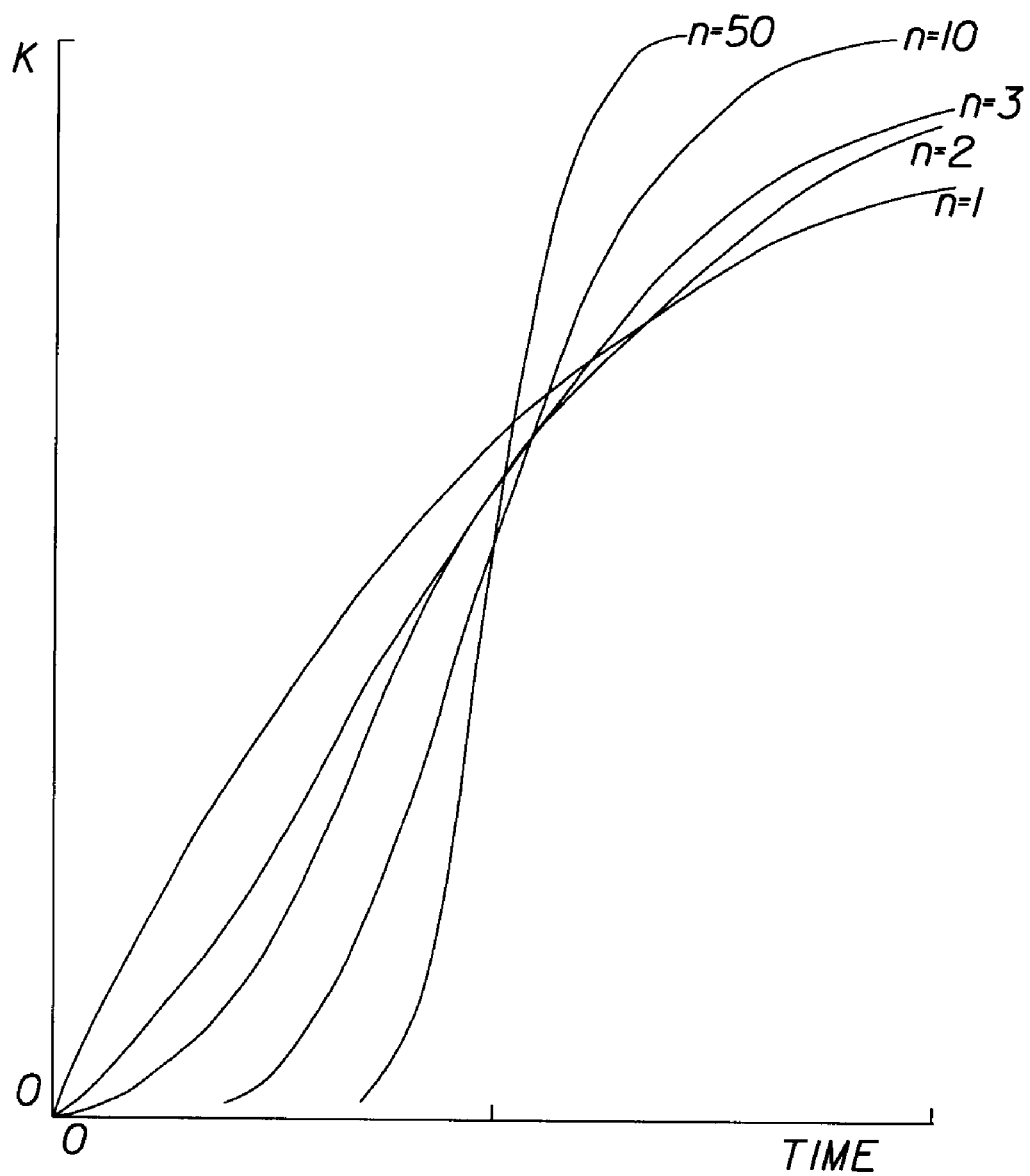
FIG. 8B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook*, Sixth Ed., Chap. 22 (McGraw Hill, Inc. 1984). As shown in FIG. 8B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 7A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, in this example, the discontinuous responsive system includes a system that has two states such as on or off When a threshold quantity of an input such as bodily waste is present in the disposable treatment article, the responsive system may perform a single responsive function upon the object to be treated. Thus, the discontinuous responsive system may perform a one-time "switch-like" function that changes from one state to another in the presence of a threshold level of an input.

Figure 7B:
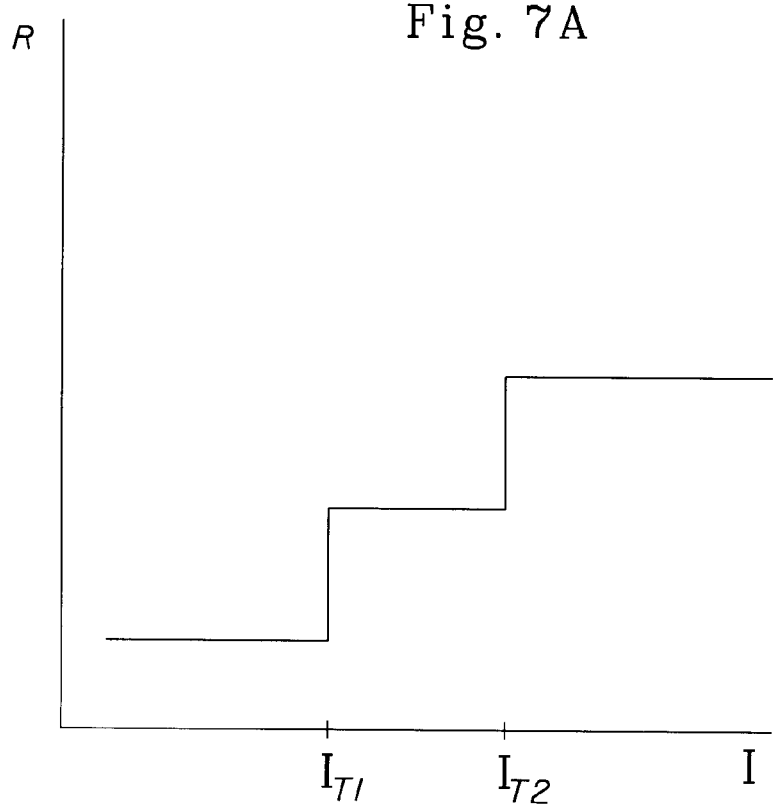
FIG. 7B shows an ideal output function of a discontinuous responsive system of the present invention having multiple threshold levels.

Alternatively, as shown in FIG. 7B, the responsive system may have multiple threshold levels at which when each threshold level is met the system may release a given "quanta" of energy or deliver a quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s), or may perform a first responsive function (e.g., inflate or expand a storage component of the article or deliver a pH buffer) at the first threshold level and perform another responsive function (e.g., delivering a quantity of enzyme inhibitor(s)) at the second threshold level. In each transition region, the responsive system responds essentially the same as the transition region in the single threshold embodiment described above.

In addition, a responsive system may monitor multiple inputs and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

The responsive system may also comprise a "closed loop" or an "open loop" system. A "closed loop" system, which is also referred to as a "feedback control loop" system, includes distinct sensor 60 and actuator 70 components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator 70 has had the opportunity to perform a responsive function on the input condition. For example, if the sensor 60 is monitoring pH on a surface or other object to be treated and a contaminant is discharged into the article 20 changing the pH of the system, i.e., the output condition of the responsive system, the responsive system may release a predetermined quantity of a pH buffer to bring the pH of the system back to the desired target pH or pH range or may release a buffer until the pH returns to the target pH or the pH range. An absorbent material such as a super absorbent polymer that continually absorbs a liquid input until the liquid has all been absorbed or the capacity of the polymer has been reached, however, is not considered to comprise a closed loop system because the absorbent material does not have distinct sensor 60 and actuator 70 components. The responsive function may be performed when the output condition reaches a threshold level, or may be performed only when the output condition and one or more other conditions are met. Acting upon the input may include acting upon the element sensed, e.g., sensing pH and acting upon the pH, or may include acting upon a composition of which the element sensed is an integral component, e.g., sensing a fecal enzyme or fecal moisture and acting upon feces. As described above, a feedback control loop system includes at least two distinct components: the sensor 60 and the actuator 70. The sensor 60 detects an event, or a parameter associated with that event. The actuator 70 receives a signal and performs a responsive function on the input condition detected by the sensor 60. The feedback control loop may further include a controller 80. In this case, the sensor 60 may provide a signal to the controller 80, and the controller 80 may direct the actuator 70 to perform a responsive function upon the input condition. The controller 80 may be a separate component of the responsive system or the controller function may be performed by the sensor 60 and/or the actuator 70.

The feedback control loop may be "non-modulating" or "modulating." In a "non-modulating" feedback control loop responsive system the responsive system acts as a one-time switch in which the actuator performs a responsive function on the input when the threshold level of the output condition is met. For example, the sensor 60 may detect a specific enzyme, and the actuator 70 may release a an enzyme inhibitor in response that acts upon the enzyme detected in the contaminant. Alternatively, the sensor 60 may detect a liquid contaminant and release a compressed foam or absorbent material in response that draws the moisture into the material as it expands. The sensor 60 may also detect a volatile gas that produces an offensive odor, and the actuator 70 may release a deodorant in response that eliminates the odor of that volatile gas. In each of these examples, the actuator 70 acts upon the input detected by the sensor 60. If the sensor 60 detects a liquid contaminant and the actuator 70 releases a compressed foam material to create a shaped void of sufficient volume to contain feces, however, the actuator 70 acts upon something other than the input detected by the sensor 60, i.e., acts upon the feces instead of the urine and is therefore not a feedback control loop. A "modulating" feedback control loop, however, includes a sensor 60, an actuator 70 and a controller 80. In a modulating feedback control loop, the output condition is monitored constantly or repeatedly, and the controller 80 directs the actuator to perform a responsive function on the input in order to maintain the output condition at a desired set point or within a desired range. A modulating responsive system may constantly or repeatedly measure pH in waste and release a given quantity of a pH control agent (such as a pH buffer or a pH decreasing agent) each time the pH of the waste is detected above a threshold pH level to provide a feedback control loop responsive system.

An "open loop" system, however, is a system that responds to the input to perform a responsive function without using feedback, i.e., the output has no effect upon the sensed input entering the system. An open loop system may include a responsive system that has a single device that performs the functions of both the sensor 60 and the actuator 70 or may have distinct sensor 60 and actuator 70 components in which the actuator acts upon something other than the input. A super absorbent polymer placed in a disposable absorbent article, for example, provides an open loop response because the polymer only includes a single device that performs the functions of the sensor 60 and actuator 70. Alternatively, an open loop responsive system may include a sensor 60 that detects a contaminant, and an actuator 70 that performs a responsive function in a continuous or a discontinuous manner on something other than the input detected by the sensor 60. For example, the sensor 60 may detect a separately applied disinfectant or cleaning agent, and the actuator 70 may capture or store the contaminant. One example of a continuous open loop responsive system in which an inflatable spacer inflates to provide a void volume to store feces via a stoichiometric chemical reaction when a liquid such as urine contacts a gas evolving material, i.e., a continuous responsive system, is described in U.S. Pat. No. 5,330,459 entitled "Disposable Absorbent Article Having An Inflatable Spacer," issued to Gary D. Lavon et al. on Jul. 19, 1994, which is incorporated herein by reference.

The present invention includes responsive systems that provide a discontinuous response, whether open loop or closed loop. The present invention also includes responsive systems that provide a continuous response and also include a feedback control loop (i.e., a closed loop system). Each of these types of responsive systems provide distinct advantages over the continuous open loop responsive systems known in the art.

Figure 9A:
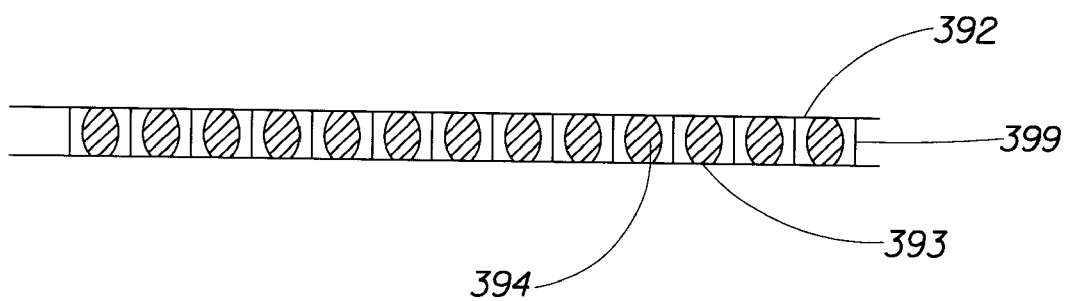
FIGS. 9A, 9B and 9C show a sectional view of an embodiment of a responsive system including a mechanical pump of the present invention.
Figure 9B:
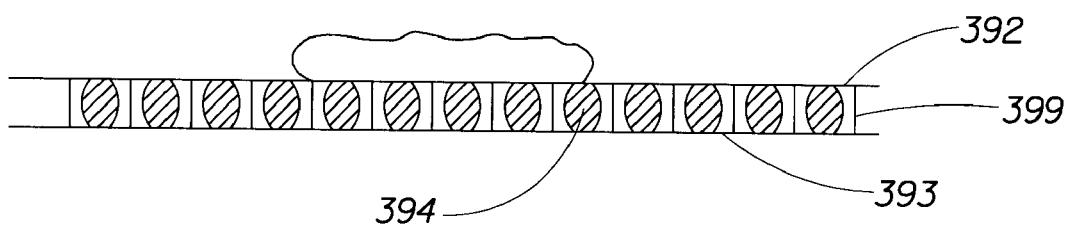
Figure 9C:
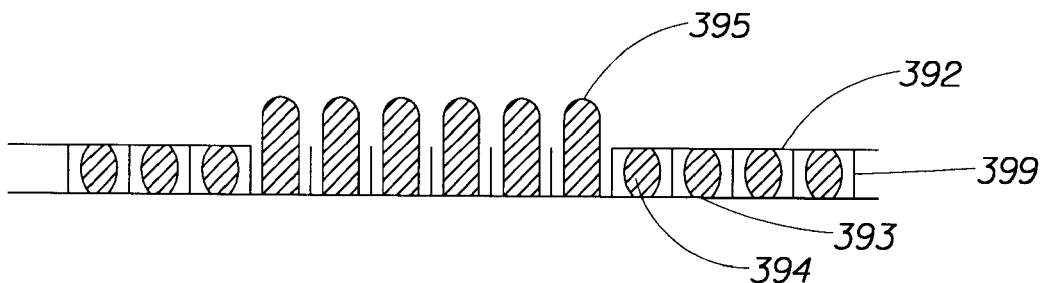

In one embodiment of the present invention, a disposable treatment article comprises a contaminant isolation device, such as a compressed resilient material that is held in compression within a bag, at least a portion of which is water soluble. Preferably, the compressed resilient material is held in vacuum compression within the bag. When a threshold level of moisture dissolves a portion of the water soluble region and discontinuously releases the vacuum, the compressed material expands and may perform a responsive function on one or more contaminants. The compressed material, for example, may be a resilient plastic foam that has a shaped void of sufficient volume to capture solid contaminants. In this embodiment, if the soluble bag responds to contamination of contaminant-derived moisture and the isolation device captures solid contaminant in response to the moisture as shown in FIG. 1, the responsive system comprises a discontinuous closed loop responsive system because the system acts upon the sensed input in a discontinuous manner when a threshold level of the input is present. If the soluble bag responds to humidity, however, the responsive system comprises a discontinuous open loop system because the responsive system acts upon something other than the input, i.e., the system captures the contaminant instead of humidity. Alternatively, the compressed material may be an absorbent material that functions as a pump by drawing fluid into its body as it expands. As shown in FIGS. 9A through 9C, for example, a high porosity, large cell, resilient foam 394 as described above may be compressed and contained in a film, envelope, bag or capsule having at least a soluble portion 392 and an insoluble backing 393. FIG. 9A shows an exemplary mechanical pump of the present invention. FIG. 9B shows feces on the structure, and FIG. 9C shows the structure after the feces is absorbed. Preferably, each cell comprising the compressed foam is individually held under vacuum. When a liquid (e.g., a liquid contaminant such as urine or other body fluid) contacts the soluble film, the film dissolves and allows the compressed foam in the cells contacted by the contaminant to expand and draw fluid into the foam as it expands. In one embodiment, the absorbent material may include multiple cells that are individually vacuum sealed in order to maintain a suction with overlying waste. In this embodiment, if the responsive system pumps the fluid that is detected by the soluble material, the responsive system comprises a discontinuous closed loop responsive system because the system acts upon the input detected by the sensor. The compressed material may alternately or additionally deliver an active agent (such as described above) to the surface as it expands.

The sensor 60 may be integral with the article 20, or may be installed by the caretaker or the wearer. The sensor 60 may be completely contained within the article such as article 20 or may have a receiving portion located in the article such that it will come into contact with the desired input and another portion such as a transmitting portion located either in the article or outside the article. The sensor 60 may be external to the article 20 yet operatively connected to some portion of the article 20 such that the sensor 60 may detect an input external to the article 20 and provide a signal to a controller 80 and/or an actuator 70. In some embodiments, the sensor may be separate from the article, e.g., separately applied to some portion of the wearer, and/or may have one or more component separate from the article.

Figure 2:
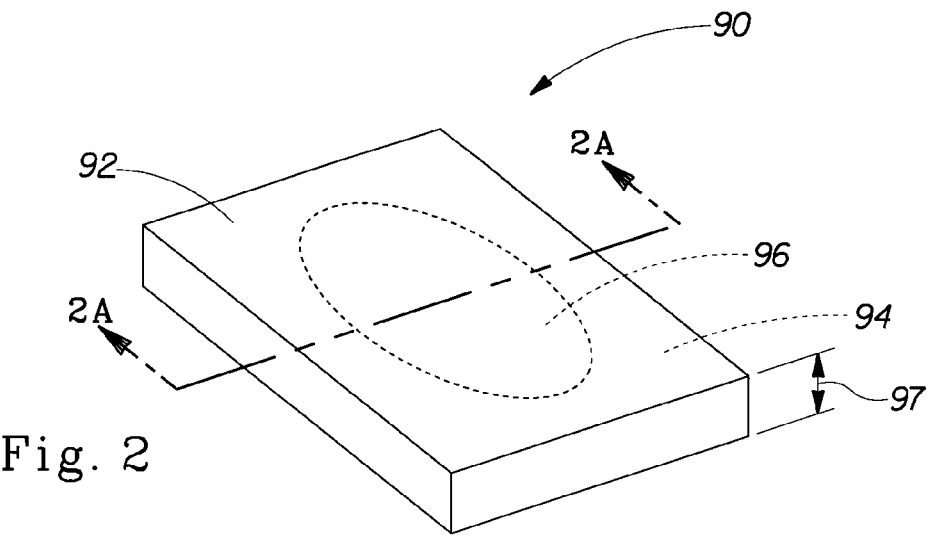
FIG. 2 shows a perspective view of a contaminant isolation device of the present invention in a compressed state before activation.
Figure 2A:
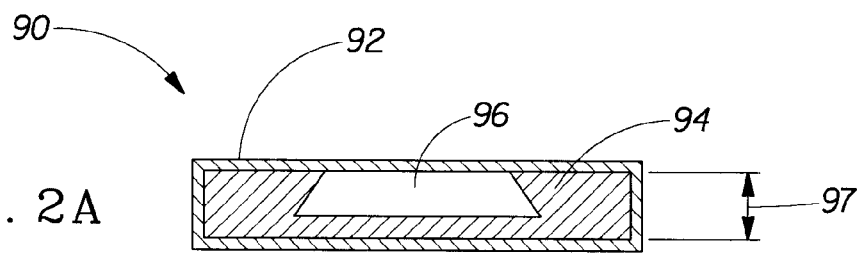
FIG. 2A shows a sectional view taken along line 2A—2A of FIG. 2.
Figure 3:
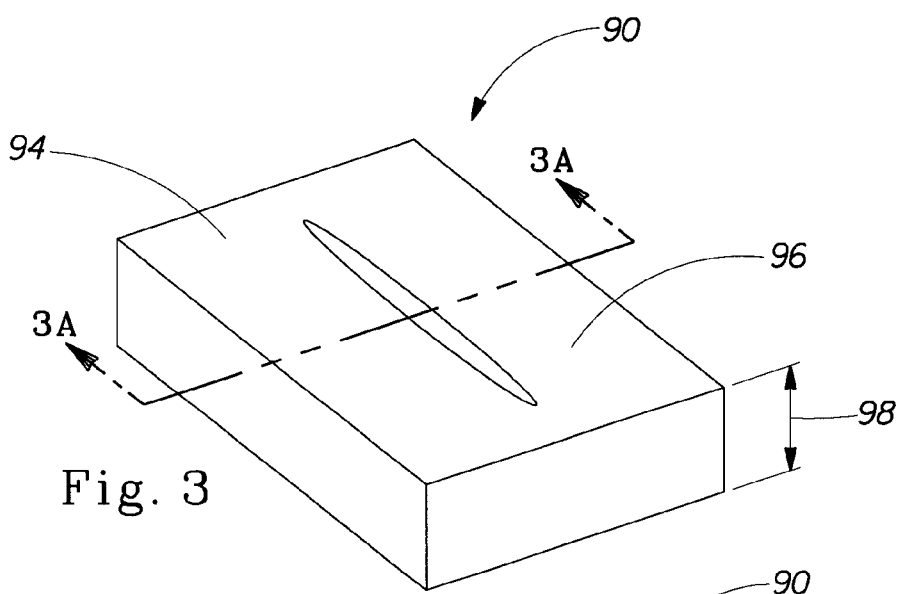
FIG. 3 shows a perspective view of one embodiment of FIG. 2 after activation.
Figure 3A:
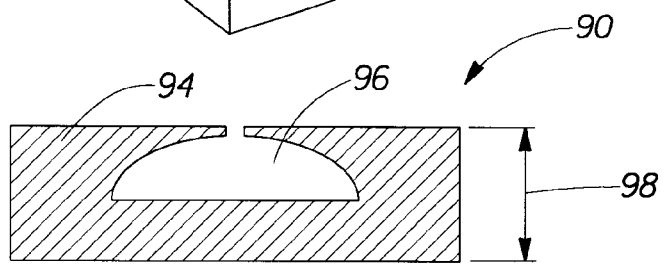
FIG. 3A shows a sectional view of FIG. 3 taken along line 3A—3A of FIG. 3.
Figure 4:
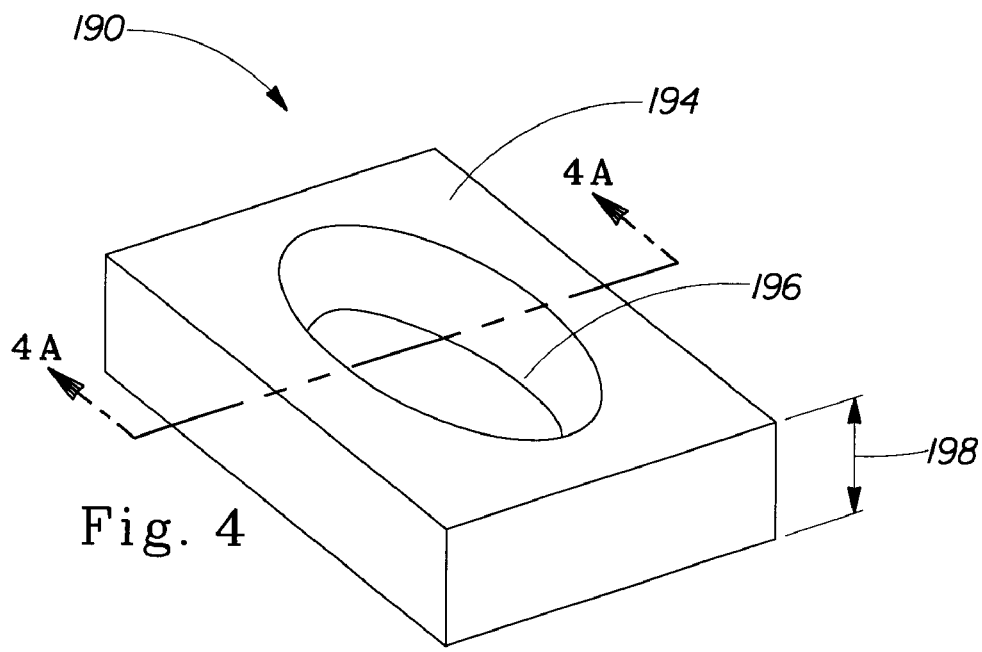
FIG. 4 shows a perspective view of an alternative embodiment of FIG. 2 after activation.
Figure 4A:
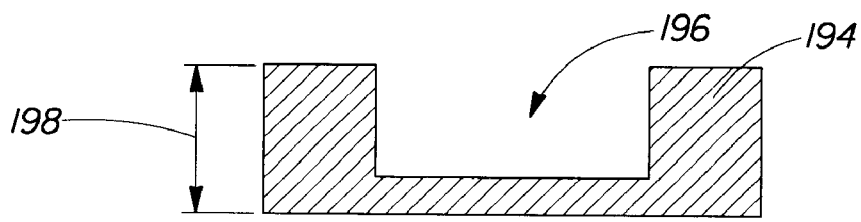
FIG. 4A shows a sectional view of FIG. 4 taken along line 4A—4A of FIG. 4.
Figure 5:
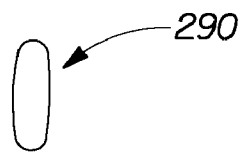
FIG. 5 shows a perspective view of an embodiment of the present invention including a soluble capsule.
Figure 6A:
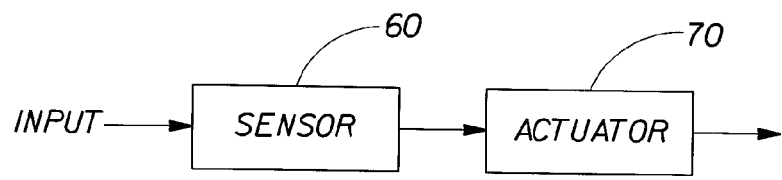
FIG. 6A shows a block diagram of an exemplary open loop responsive system.
Figure 6B:
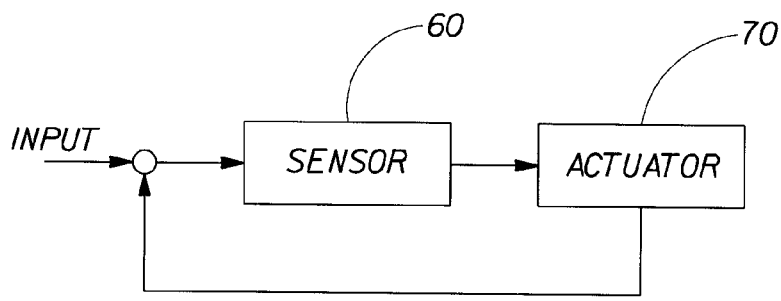
FIG. 6B shows a block diagram of an exemplary closed loop responsive system.
Figure 6C:
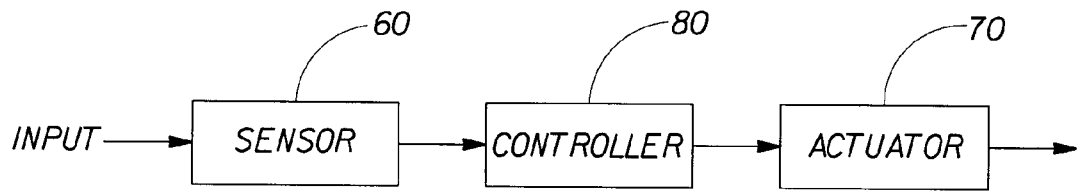
FIG. 6C shows a block diagram of an exemplary open loop responsive system including a controller.
Figure 6D:
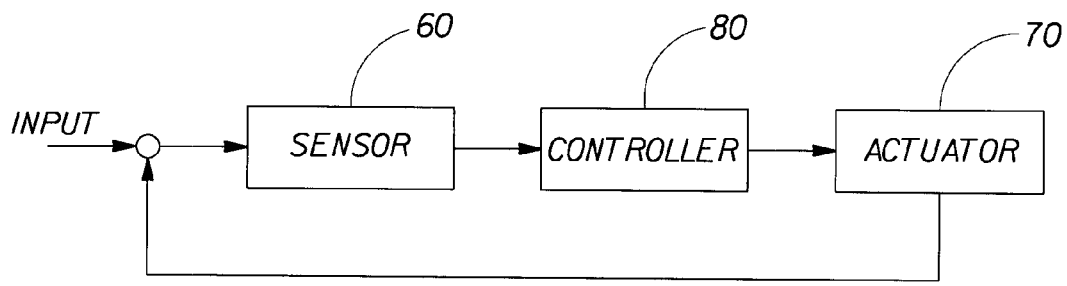
FIG. 6D shows a block diagram of an exemplary closed loop responsive system including a controller.

Embodiments of the present invention may also include retaining regions for receiving and containing materials to be removed by articles of the present invention, including without limitation liquids, semi-liquids, and solids. Examples of such retaining structures include tanks, pockets within an absorbent structure (e.g. comminuted wood pulp or other absorbent material), barriers for limiting the movement of retained materials in the article, voids, and compartments which accept and contain materials deposited in the article, and the like, or any combinations thereof In the contaminant isolation device embodiment shown in FIGS. 2 and 3, the compressed material 94 may comprise any elastic foam that has suitable compression and recovery properties so that it is capable of being compressed and held within the bag 92 and also capable of recovering a substantial proportion of its original height, preferably at least about 75%, after release of a constraining force. At least a portion of the bag 92 comprises a soluble region or a soluble seal. The soluble region or seal may dissolve in contact with the contaminant or with other material that is associated with or predictive of the contaminant, for example, water, urine, fecal enzymes, bacteria, etc. The bag 92 preferably retains the compressed material 94 in a vacuum compression state until a portion of the soluble region of the bag 92 dissolves enough (i.e., a threshold level of water is detected) to discontinuously release the vacuum. Once expanded, the foam is also preferably rigid enough to withstand the pressure or forces applied to it during use so that the foam will not compress significantly, preferably less than about 50%, and release the captured contaminant. An EVA foam, for example, such as the ones available from Foamex Corporation of Eddystone, Pa. identified as SIF/210PP1 or Aquazone 80A foam, or from Sentinel Products Corporation of Hyannis, Mass. identified as MC1900 EVA 2 lb/ft$^3$, or a foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very. High Water-To-Oil Ratios" issued to DesMarais et al. on Jul. 22, 1997 may be used as the feces capture compression material 94. As shown in FIG. 2, the compression material 94 may include an aperture that is open when the compression material 94 is compressed. When the compression material 94 expands, the aperture may be enclosed by the perimeter of the compression material 94 as shown in FIG. 3. This allows the waste to be captured or encapsulated away from the user or surface or an object being treated inside the aperture of the compression material. Alternatively, as shown in FIG. 4, the compression material 94 may have an open aperture that acts as a spacer and provides a void space having a sufficient volume to store contaminants in the article 20. This allows the compression material 94 to receive and capture contaminant a multiple number of times including after the compression material 94 has expanded.

The bag 92 may be soluble in the presence of one or more different types of input, such as water, body fluids, fecal enzymes, a pH level, etc., and may have physical and/or chemical characteristics (e.g., thickness) that may be designed to set a threshold level of that input required to dissolve the bag. The soluble bag 92 may, for example, comprise a plastic film that is soluble to water such as a PVA film supplied by Chris-Craft Industrial Products, Inc. of South Holland, IL as MONOSOL M7031 film, or H. B. Fuller Company of St. Paul, Minn. as HL 1636 or HL 1669-X. The film thickness, for example, may also be modified to provide a desired activation. IS The film used may, for example, also have a thickness in the range from about 0.0005 to about 0.0015 inches. An HL 1636 film having a thickness of about 0.001 inches, for example, will activate with a moisture content of about 0.049 grams per square inch.

In this embodiment, the isolation device 90 operates as a non-modulating, discontinuous responsive system. The soluble portion of the bag 92 acts as a sensor that responds to a specific input. The sensor may, for example, be responsive to water in the contaminant or spill or another component in the object to be isolated, e.g., an enzyme in feces. When any soluble portion of the bag 92 contacts a threshold level of the input, the soluble portion of the bag 92 dissolves and releases the compression material, which expands to capture, surround or envelop the contaminant. The physical and chemical characteristics of the material used to form the bag 92 define the threshold level of the input and act as a controller that determines when the compression material 94 is to be released. When the bag dissolves, the release of the vacuum and the expansion of the compression material 94 function as an actuator to capture the contaminant. Thus, the isolation device 90 acts as a one-time discontinuous switch that releases the stored mechanical energy of the compression material 94 when a threshold level of a given input is detected. The useful energy of the responsive system includes: (stored energy)−(hysteresis loss). The compression material 94 used preferably has a minimal hysteresis loss and a maximum recovery. More preferably, the compressive hysteresis loss is less than about 25% so that the recovery upon release is at least about 75%.

In an alternative responsive system, compression devices similar to FIGS. 2 and 3 are provide, except that the compression material when it expands does not form a void but instead releases a material (e.g., an active agent) for treating an object, wherein the active agent is stored in or on the compression material. Upon activation of the compression material the active material is released in order for it to perform its intended function. This type of compression device can be referred to a compression-active material release device, and can used in conjunction with a sensor as described above.

A continuous closed loop embodiment of the present invention may comprise a pH sensitive, water soluble film that forms an envelope around a pH buffer system. The soluble material described above may be pH-sensitive. As such, the soluble material may have a pH threshold. The "pH threshold" of a soluble material is the pH at which the material changes from soluble to insoluble or vice-versa. For example, the soluble material may be substantially insoluble at pH of less than 6, but soluble at a pH of greater than 6. Thus, the pH threshold of that material is a pH of 6. In preferred embodiments of the present invention, the pH threshold of the soluble material is preferably between about 5 and about 9, and preferably between about 5.5 and about 8.5, although other pH thresholds are contemplated. The change in pH may be the cause or trigger for the dissolution of the soluble material, or it may also be used to help increase or decrease the rate of dissolution of the contaminant passage member. Thus, the performance of the contaminant passage member can be varied depending on factors such as the type and amount of contaminant. A contaminant passage member suitable for bodily waste and other purposes is further described in U.S. application Ser. No. 09/106,423, entitled "Directionally Preferential Waste Passage Member For Use With Disposable Absorbent Article" filed on Jun. 29, 1998, which is incorporated by reference herein. The pH sensitive film suitable may have, for example, a pH threshold in the range of about 5 to 7. The pH buffer, for example, may be a pH 7 phosphate buffer available from Corning, Inc., Corning, NY (Cat #473650). When the threshold pH. is reached, the pH buffer is released and functions in a continuous manner via a stoichiometric chemical reaction. The system is closed loop because the system detects pH and acts upon the pH, i.e., the input.

This embodiment may further comprise an open loop responsive system or a feedback control loop responsive system. If the bag 92 dissolves in water and the device 90 captures contaminant (such as feces, for example), the responsive system comprises an open loop system because the output of the system, i.e., the contaminant, does not affect the input, i.e., the water. If the bag responds to contaminant (e.g., fecal moisture or a fecal enzyme), however, the responsive system comprises a feedback control loop because the system uses a measure of the output. In this example, the feedback control loop responsive system is non-modulating because it acts as a one time switch and does not continually or repeatedly alter the input to maintain a desired set point level for the output.

In another embodiment of the present invention, a foam such as described in the above example or another resilient material may be twisted creating torsional mechanical potential energy and enclosed in a soluble film envelope, bag or capsule as described above. Preferably, the twisted resilient material is held in the twisted position in the soluble film, envelope, bag or capsule under vacuum. In this embodiment, when a threshold level of moisture, pH, etc. is detected the film or capsule dissolves, discontinuously releasing the vacuum, and releasing the foam. The stored torsional mechanical potential energy causes the foam to unwind and may perform a responsive function such as storing, capturing or entrapping contaminants, wiping the surface of an object, applying an active agent to an object, etc. In this embodiment, the responsive system provides a non-modulating, discontinuous response. Because the system acts on something other than the input, i.e., it acts upon the skin of the wearer, the responsive system comprises an open loop system.

In yet another embodiment, a pH control agent may be embedded in a film or granules, or held under a film of a pH-sensitive material that is insoluble, i.e., a solid, below a predefined pH (e.g., less than a pH of about 6.0), but soluble above that pH level. Upon detection of the threshold pH level or above, the pH-sensitive embedding or overlying material dissolves, releasing the pH control agent to treat the intended object. In the case of the embedded pH control agent, the responsive system releases the agent in a continuous manner as the embedding material dissolves. In the case of the pH control agent being held under a film, the responsive system releases the agent in a discontinuous manner after the film has dissolved. A pH control agent may be a buffer, a pH decreasing agent, e.g., an acid, or a pH increasing agent, e.g., a base. A variation of this embodiment may include a substrate that will result in a pH change upon hydrolysis by one or more target enzymes or other component that may be present in a contaminant. When the target enzyme or other component reacts with the substrate, the reaction creates a pH change that may react with a pH sensitive material similar to the one described above to release a pH control agent. An enzyme inhibitor may also be embedded in the pH-sensitive material. Presence of the target enzyme, e.g., a fecal enzyme, may result in the conversion of the substrate and a change in pH, resulting in the dissolution of the pH-sensitive material and release of the enzyme inhibitor to treat the feces or other object, such as the user's skin or other surface. Exemplary pH sensitive materials are known in the art and include polyacrylamides, phthalate derivatives, formalized gelatin, shellac, keratin, cellulose derivatives, e.g., oxidized cellulose, and polyacrylic acid derivatives. Preferred materials include cellulose acetate phthalate, vinyl acetate, polyvinyl acetate phthalate, hydroxy propyl methyl cellulose phthalate and poly methacrylate blended with acrylic acid and acrylic ester copolymers. Other exemplary materials are described in EP612,520 A2 entitled "pH Triggered Osmotic Bursting Delivery Devices," which is incorporated herein by reference.

A further embodiment of a responsive system of the present invention may deliver, i.e., actively transport, an agent to an object to be treated, including an input, a contaminant, a wearer, a user, or an article of which the input is a component to perform a responsive function. In this embodiment, for example, the actuator 70 may comprise a compressed resilient foam or a closed system liquid transport member that delivers an agent to the object to be treated when the sensor detects a the input.

The embodiments of the present invention listed above that release or deliver pH control agents in response to the dissolving of the pH sensitive material comprise a responsive system having a feedback control loop that acts upon the pH level after a threshold pH level has been reached. These embodiments may be either modulating s or non-modulating. If the pH control agent released, for example, is a buffer that contains both pH increasing and pH decreasing components, the system comprises a modulating feedback control loop system that will continually monitor the pH in the article and will maintain the pH level in the article at the desired set point or within a target range of the buffer whether the pH is raised or lowered. If the responsive system, however, releases only a pH decreasing agent at the first pH threshold level, for example, the system comprises a non-modulating feedback control loop system because the pH decreasing agent will lower the pH of the system until the agent is exhausted and will not maintain the pH of the system at a desired pH level or within a target pH range. If, however, it is known that the contaminant contacting the article will raise the pH level, and the system releases a predetermined quantity of a pH decreasing agent each time the pH level in the article reaches a threshold pH level, the system may comprise a modulating feedback control loop system because it will repeatedly release the pH control agent whenever the pH of the article is above the desired set point of the system. The examples listed above that release or deliver an agent that acts upon something other than the pH level (e.g., a fecal enzyme inhibitor) in response to the pH level reaching a threshold level, however, comprise open loop responsive systems. In these examples, the responsive system releases an agent that does not affect the input condition being monitored, i.e., the pH level.

The article of the present invention may also release or deliver as a responsive function one or more feces modifying agents ("FMA's"), "viscous bodily waste modifying agents", "modifying agents" or "agents"), such as when fecal mater is sensed by the sensor or an input indicating the impending occurrence of a fecal event. The FMA is used at an effective amount for modifying the chemical or physical properties of viscous bodily waste, such as feces and menses. This can include hardening the fecal matter, increase or decrease the effective viscosity of feces, increase or decrease the ease of dewatering the feces, decrease the stickiness of the feces, decrease the adhesion characteristics of the feces, or any combination of the above.

An "effective concentration" of an FMA, as used herein, refers to the relative amount of the agent required to have a measurable effect on the viscosity or hardness of the fecal matter. Preferably, a concentration of an FMA of at least about 0.01 weight percent of the feces to be treated is desirable, and more typically between about 0.1 and about 50 weight percent of the feces is available to the feces.

The Feces Modifying Agent of the present invention may include one or more "water liberating" agents capable of separating the liquid portion of the feces (i.e. water) from the solid structure of the feces and/or reducing the degree of "binding" of the feces water to the solid feces components.

Feces Modifying Agents which act to decrease the viscosity of feces as described above include, but are not limited to the following organic and inorganic flocculants, and the like. Inorganic flocculants include but are not limited to divalent and trivalent metal salts, including but not limited to salts of iron, aluminum, calcium, and sodium and mixtures thereof It is believed that such salts form hydrolysis products which associate with the charged surfaces of the particulate matter in the feces colloidal structure, resulting in flocculation (i.e., flocculation via any of the mechanisms described above). Some examples include ferrous chloride, ferric chloride, aluminum sulfate, aluminum chloride hydroxide, sodium aluminate, calcium sulfate, poly-aluminum-silicate-sulfate (available from Handy Chemical, Quebec under the trade name PASS), ferrous sulfate, calcium carbonate, and the like.

Organic flocculants include but are not limited to natural substances like albumin, xanthan gum, and guar gum. Synthetic flocculants are generally non-crosslinked, water-soluble molecules or polymers and may include acrylic and acrylamide polymers and their derivatives (in very low concentrations (a few hundredths of a weight percent)), polyvinyl pyrrolidone, poly methacrylates, polyamines, polyethylene oxide, and allylamine polymers. Preferably, these are cationic polymeric species. (Although applicants do not wish to be bound by theory, it is believed that these agents function by associating with the negatively charged regions of the feces particulate fraction and reducing the net inter-particle repulsive charge.) Some of the synthetic flocculants may act to increase the viscosity of aqueous solutions if used in high concentrations and will be discussed below as feces thickening agents. It is also important to note that if some of the organic flocculants are used in too high a concentration their effect may be reversed. Thus, the water may be held more tightly by the feces due to the tendency of these agents to form gels if used in excess of the amount necessary to associate with the charged particulates.

Some crosslinked derivatives of the synthetic organic flocculants (e.g., polyacrylates), or derivatives thereof, are known in the art as superabsorbent polymers, and function to form water-insoluble gels upon contact with very low viscosity aqueous wastes such as urine and menses. However, because these crosslinked species cannot readily dissociate (i.e., dissolve) and adsorb to the particulate species within the feces matrix, they do not function as flocculants.

Feces Modifying Agents which act to decrease the viscosity of feces as described above may also include reducing agents. For example, agents that reduce disulfide bonds (—S—S-bonds) as found in colonic mucous colomin mucous generally comprises (macromolecular glycoproteins linked by disulfide bonds) can effect a significant viscosity reduction in feces having high mucous content. While not wishing to be bound by theory, it is believed that reduction of the mucin disulfide bonds (which function as crosslinks between mucin polymer chains) significantly reduces the average molecular weight of the glycoprotein structure in feces such as runny feces to a level well below the "gel point" of the mucin (i.e., long-distance structure becomes impossible due to the relatively small size of the glycoproteins). Exemplary reducing agents include sulfites such as sodium hydrogensulphite, sodium sulfite and sodium dithionite, thiols and thiol alcohols (e.g., 2-mercaptoethanol, dithiothreitol, and dithioerythritol), mercaptoacetic acid, sodium thioglycolate, thiolactic acid, thioglycoamide, glycerol monothioglycolate, borohydrides (e.g., sodium borohydride), ternary amines, thiocyanates such as sodium thiocyanate, thiosulfates such as sodium thiosulfate, cyanides such as sodium cyanide, thiophosphates such as sodium thiophosphate, arsenites such as sodium arsenite, phosphines such as triphenyl phosphine, phenols such as thiophenol and p-nitrophenol, betaines, and others including, but not limited to, lithium aluminumhydride, aluminum chloride, guanidine hydrochloride, stannous chloride, hydroxylamine, and $LiHB(C_2H_5)_3$.

In other particularly preferred embodiments of the present invention, modifying agents which generally increase the structure of the feces by increasing the degree of water binding are employed to increase the viscosity and reduce the mobility of the feces. This may be accomplished via the use of thickening agents in the appropriate concentrations. Thickening agents may be natural or synthetic and are generally water-soluble, (typically non-crosslinked) polymers, such as CMC (carboxymethyl cellulose), hydroxypropyl methylcellulose, hydroxyethyl cellulose, polyacrylic acid and its derivatives, carageenan, polyacrylamide and its derivatives, (polyethylene)imines, gums (such as xanthan, guar, karaya, agar, locust bean gum, pectin, and gum ghatti, or mixtures thereof) and other similar materials. Cationic polymers are preferred due to the anionic surfaces of fecal bacteria and biopolymers. Thickening agents increase the viscosity of the feces by dissolving in the free water in the feces and osmotically "binding" water, thereby increasing the solid "structure" of the feces. Generally, large, insoluble polyelectrolytic polymeric particles such as conventional superabsorbents are not able to dissolve in the feces free water and create a matrix within the feces at the molecular level. Some FMAs may perform differently on different types of feces (e.g., a FMA that acts as a flocculent on one type of feces, may act as a thickening agent on another type due to variance in the structural character of the specific type of feces). One example of this is calcium hydroxide which functions as a flocculant for a runny fecal analog, but as a thickener for a pasty fecal analog in the same concentrations.

In still other preferred embodiments, the modifying agent comprises an ionic complexing agent. Ionic complexing agents may include any single component which complexes with itself or water or other chemical entities in the feces to form regions of increased structure and rigidity within the feces. The resultant complex acts to stabilize or bind water more tightly in the feces. Exemplary ionic complexing agents include ZnO, MgO, MnO, CaO, calcium hydroxide, $Al_2O_3$, aluminum salts, zinc salts such as zinc acetate and zinc glucanate, gelatin, quaternary ammonium salts, ethanolamines, alginic acid, cetyl trimethyl ammonium bromide and the like). Alternatively, the ionic complexing agent may comprise a two (or more) component system, wherein the complex (i.e., longer-range structure) is created by the interaction of the two added components (e.g., aluminum, calcium, or zinc salts plus alginic acid and/or salts thereof). The ionic complexing agents may form crystal hydrates when complexing with water, In general, calcium-containing compounds or systems (e.g., CaO, calcium hydroxide, and calcium alginate, etc.) are some of the most effective feces modifying agents.

In various embodiments, the FMA may be organic or inorganic, a low molecular weight molecule or polymeric in nature, and/or may be a liquid, solid (e.g., powder, fiber, film, web), or a semi-solid, or combinations thereof The FMA may be presented in a water/oil or oil/water emulsion, a suspension, or mixture. In another embodiment, a sufficient quantity of water containing electrolytes (e.g., from liquid contaminants or feces) may be detected by an electrical sensor when the electrolytic water completes a circuit, i.e., as a switch, causing current from a stored energy source such as a battery to initiate a chemical reaction such as a phase transition, etc. For example, the current may be applied to an electrically sensitive gel and cause it to change geometry and create void space for contaminants in the article. Again, this embodiment comprises a discontinuous responsive system that may be an open loop or a feedback control loop system depending upon whether the input sensed is being affected by the responsive system. If the sensor detects moisture in a liquid contaminant, urine for example, the responsive system that creates a void space for receiving feces comprises an open loop system. If the sensor detects fecal moisture, however, the responsive system comprises a feedback control loop system because it acts upon the input being sensed. In this example, the feedback control loop system may further comprise a modulating system if the void space captures the fecal moisture along with the feces, the moisture evaporates or is drawn away from the sensor element, thereby opening the circuit, and the controller activates another void space when the sensor detects fecal moisture again.

In a further embodiment of the present invention, an absorbent material that swells when absorbing a liquid may be used as a sensor that, when a threshold level of swelling has occurred, mechanically closes a pair of electrical contacts in order to complete an electrical circuit. In this embodiment, the electrical circuit may trigger an actuator in a discontinuous manner to perform a responsive function on the bodily waste, the wearer, the article or any component or components thereof For example, the actuator may open a valve to allow the liquid to flow to another portion of the article, pump the liquid to another portion of the article, initiate a change in geometry in an electrically sensitive gel to change geometry and create a void space, release a skin care composition, a pH control agent or a deodorant, etc.

A material such as a fiber, film, nonwoven or other cellular structure may also be restrained in a given configuration by a material that responds to a contaminant, such as a solid contaminant (e.g., bodily waste such as feces), or a component of that contaminant. When the solid contaminant contacts the restraining material, the restraining material may release the fiber, film, nonwoven or other cellular structure to capture or isolate the contaminant away from an object, such as a surface (e.g., of a floor or other hard surface, or a user's or wearer's skin). An elastic barrier, for example, may be restrained at two restraint points away from a void space in an article by a material that dissolves, weakens, etc. in response to a contaminant (which may be the same contaminant being isolated or another contaminant that is associated with it). When the solid contaminant has become disposed within the void space, and the restraining material at one or both of the restraint points dissolves, the elastic barrier may contract in a discontinuous manner and cover the void space to isolate the solid contaminant.

In another embodiment, the responsive system may comprise a pH buffer embedded in a pH sensitive material that allows a continuous release of the pH buffer in a continuous dissolution in increased "non-target" pH water. As the moisture having a non-target pH level comes into contact with the pH sensitive material, the material dissolves in a continuous manner, and releases a quantity of the pH buffer, which changes the pH level of the moisture to the target pH level, i.e., the responsive system acts upon the input. As increasing quantities of moisture having a non-target pH level contact the pH sensitive material, the material releases an increasing quantity of the pH buffer. Therefore, the responsive system comprises a continuous closed loop responsive system.

In yet another embodiment, one or more enzymes or microorganisms may be detected by a sensor such as an enzyme-degradable film or capsule, or a biosensor as described above to trigger a separate actuator, e.g., an electrically operated valve, to release an enzyme inhibitor to treat the skin. Exemplary enzyme inhibitors are disclosed in U.S. Pat. application Ser. No. 09/041,266 entitled "Disposable Absorbent Article Having A Skin Care Composition Containing An Enzyme Inhibitor" filed on Mar. 12, 1998, which is incorporated by reference herein. In yet another embodiment, certain pH conditions may be detected by the use of a pH sensitive gel, which may open a valve to release a pH control agent to treat the skin. In another embodiment, a pre-defined pressure threshold is detected, resulting in the rupture of a capsule or "bubble," effecting the release of a skin care treatment agent or composition.

Exemplary skin care compositions (or lotions), are disclosed in U.S. Pat. No. 5,607,760 entitled "Disposable Absorbent Article Having A Lotioned Topsheet Containing An Emollient And A Polyol Polyester Immobilizing Agent," issued to Donald C. Roe on Mar. 4, 1997; U.S. Pat. No. 5,609,587 entitled "Diaper Having A Lotioned Topsheet Comprising A Liquid Polyol Polyester Emollient And An Immobilizing Agent," issued to Donald C. Roe on Mar. 11, 1997; U.S. Pat. No. 5,635,191 entitled "Diaper Having A Lotioned Topsheet Containing A Polysiloxane Emollient," issued to Donald C. Roe et al. on Jun. 3, 1997; and U.S. Pat. No. 5,643,588 entitled "Diaper Having A Lotioned Topsheet" issued to Donald C. Roe et al. on Jul. 1, 1997, as well as U.S. patent applications Ser. Nos. 08/926,532 and 08/926, 533, each filed on Sep. 10, 1997, each of the above listed patents and applications are incorporated herein by reference.

In a preferred embodiment, provided are disposable planar substrates, such as but not limited to tissues, towels or wipes of non-woven or woven fibrous or non-fibrous materials having responsive systems incorporated into or onto the substrate.

Fibrous substrates include natural fibers, synthetic fibers, or mixtures of natural and synthetic fibers. Suitable natural fibers include but are not limited to cellulosic fibers, such as wood pulp fibers, cotton, hemp, wool, and rayon. Suitable synthetic fibers include fibers commonly used in textiles, including but not limited to polyester and polypropylene fibers.

Various forming methods can be used to form a suitable fibrous planar substrate, alternatively sometimes referred to as a web. For instance, the web can be made by nonwoven dry forming techniques, such as air-laying, or alternatively by wet laying, such as on a papermaking machine. Other nonwoven manufacturing techniques, including but not limited to techniques such as melt blown, spunbonded, needle punched, and hydroentanglement methods may also be used.

In one embodiment, the dry fibrous web can be an airlaid nonwoven web comprising a combination of natural fibers, staple length synthetic fibers and a latex binder. The dry fibrous web can, for example, be about 20–80 percent by weight wood pulp fibers, 10–60 percent by weight staple length polyester fibers, and about 10–25 percent by weight binder. p The dry, fibrous web can, but without limitation, have a basis weight of between about 40 and about 80 grams per square meter. The density of the dry web can be, for example, less than about 0.12 grams per cubic centimeter. The density is the basis weight of the dry web divided by the thickness of the dry web, measured in consistent units, and the thickness of the dry web is measured using a circular load foot having an area of about 2 square inches and which provides a confining pressure of about 95 grams per square inch. In one embodiment, the dry web can have a basis weight of about 64 grams per square meter, a thickness of about 0.06 cm, and a density of about 0.11 grams per cubic centimeter.

In one embodiment, the dry fibrous web can comprise at least 50 percent by weight wood pulp fibers, and more preferably at least about 70 percent by weight wood pulp fibers. One particular airlaid nonwoven web which is suitable for use in the present invention comprises about 73.5 percent by weight cellulosic fibers (Southern softwood Kraft having an average fiber length of about 2.6 mm); about 10.5 percent by weight polyester fibers having a denier of about 1.35 gram/9000 meter of fiber length and a staple length of about 0.85 inch; and about 16 percent by weight of a binder composition comprising a styrene butadiene copolymer. The binder composition can be made using a latex adhesive commercially available as Rovene 5550 (49 percent solids styrene butadiene) available from Mallard Creek Polymers of Charlotte, N.C.

One suitable airlaid nonwoven web for use in the present invention is the airlaid nonwoven web employed in PAMPERS BABY FRESH™ brand baby wipes marketed by The Procter & Gamble Co. of Cincinnati, Ohio.

The following patents are also incorporated herein by reference for their disclosure related to webs: U.S. Pat. No. 3,862,472 issued Jan. 28, 1975; U.S. Pat. No. 3,982,302 issued Sep. 28, 1976; U.S. Pat. No. 4,004,323 issued Jan. 25, 1977; U.S. Pat. No. 4,057,669 issued Nov. 8, 1977; U.S. Pat. No. 4,097,965 issued Jul. 4, 1978; U.S. Pat. No. 4,176,427 issued Dec. 4, 1979; U.S. Pat. No. 4,130,915 issued Dec. 26, 1978; U.S. Pat. No. 4,135,024 issued Jan. 16, 1979; U.S. Pat. No. 4,189,896 issued Feb. 26, 1980; U.S. Pat. No. 4,207,367 issued Jun. 10, 1980; U.S. Pat. No. 4,296,161 issued Oct. 20, 1981; U.S. Pat. No. 4,309,469 issued Jan. 25, 1982; U.S. Pat. No. 4,682,942 issued Jul. 28, 1987; and U.S. Pat. Nos. 4,637,859; 5,223,096; 5,240,562; 5,556,509; and 5,580,423.

The planar substrate can be single ply or multi-ply, single density or multi-density, and single basis weight or multi-basis weight. Multi density and basis weight substrates are disclosed, for example, in hereby incorporated by reference.

Multi-density webs may be made by processes well known in the art. The following patents disclose suitable processes for making webs that can be used in the present invention: U.S. Pat. No.: 4,529,480, issued Jul. 16, 1985 to Trokhan; U.S. Pat. No. 4,637,859, issued Jan. 20, 1987 to Trokhan; U.S. Pat. No. 5,364,504, issued Nov. 15, 1994 to Smurkoski et al.; U.S. Pat. No. 5,529,664, issued Jun. 25, 1996 to Trokhan et al.; U.S. Pat. No. 5,679,222 issued Oct. 21, 1997 to Rasch et al.; U.S. Pat. No. 5,714,041 issued Feb. 3, 1998 to Ayers et al.; U.S. Pat. No. 5,906,710, issued May 25, 1999 to Trokhan, all commonly assigned to The Procter & Gamble Co., Cincinnati, Ohio, USA, the disclosures of which are incorporated herein by reference.

Multi-basis weight webs and methods for making them are disclosed in U.S. Pat. No. 5,503,715, issued Apr. 2, 1996 to Trokhan et al.; U.S. Pat. No. 5,614,061, issued Mar. 25, 1997 to Phan et al.; U.S. Pat. No. 5,804,281 issued Sep. 8, 1998 to Phan et al.; and U.S. Pat. No. 5,900,122 issued May 4, 1999 to Huston, the disclosures of which are incorporated herein by reference.

In one alternative embodiment, the substrate can comprise a hydroentangled web having a basis weight of about 62 grams per square meter and comprising about 50 percent by weight rayon fibers and about 50 percent by weight polyester fibers, polypropylene fibers, or a combination thereof. In another alternative embodiment, the substrate can comprise a laminate of two outer hydroentangled webs, such as nonwoven webs of polyester fibers having a basis weight of about 30 grams per square meter, joined to an inner constraining layer, which can be in the form of net-like scrim material which contracts upon heating to provide surface texture in the outer layers.

Figure 1B:
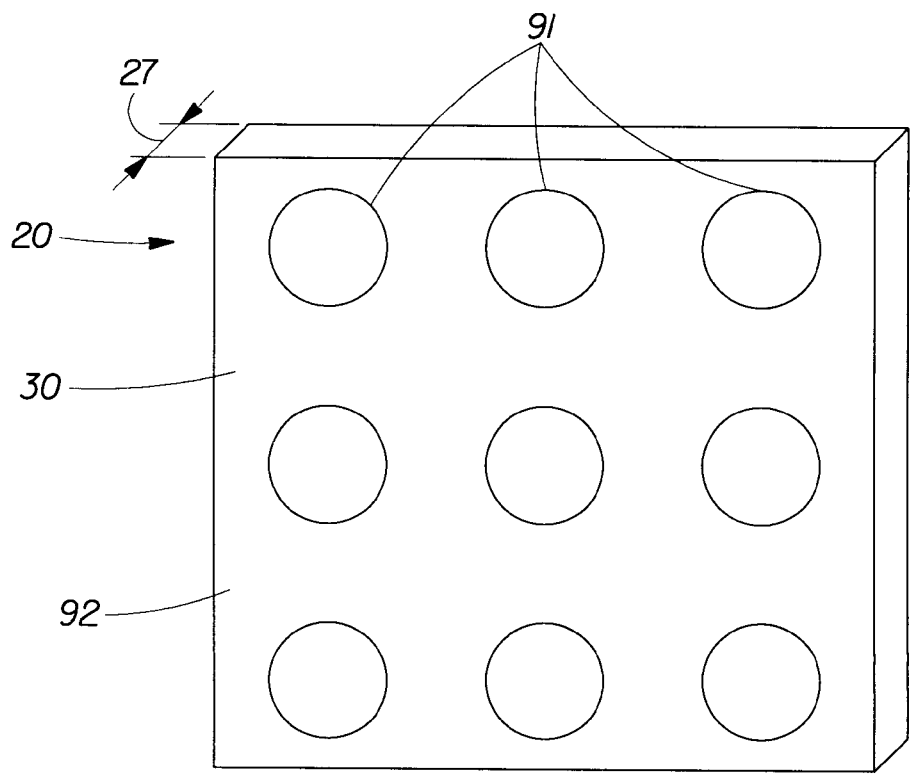
FIG. 1B is a perspective view of an article made in accordance with the present invention wherein the article is an alternate embodiment of a planar substrate.

FIG. 1A is a perspective view of an article 20 of the present invention which is a planar substrate 30 suitable for cleaning and removing contaminants from a surface, for example a baby wipe suitable for wiping feces and urine from a baby's skin. A paper towel or tissue suitable for wiping spills or bodily. Substrate 30 can be any woven or nonwoven fibrous material or open cell foam. Preferably is a fibrous material such as a cellusosic or synthetic polymeric material such as polyethylene or polypropylene, or a combination thereof The planar substrate 30 has thickness 27, which can vary depending upon intended use and materials of construction, but generally will be between about 0.05 cm and about 25 cm, more generally between about 0.1 cm and about 5 cm. Substrate 30 can be of any width and length, and can also be a continuous roll. Substrate 30 has a top face 92 with contaminant isolation device 90 disposed thereon. Containment isolation device 90 can be attached to the substrate 30 by any techniques known in the art, for example by gluing, Contaminant isolation device 90 can be as shown in FIGS. 2 and 3 and described in detail above. Containment isolation device can alternately be replaced with a compression device which releases active material, such as described above, or with other actuator device encompassed by the present invention. FIG. 1B shows an article similar to FIG. 1B except that instead of a single large containment isolation device, this embodiment shows a substrate 30 with a plurality of compression devices 91 which can be as described above in FIG. 1A.

Wipes, such as baby wipes, skin wipes, hard surface cleansing wipes, etc., as well as other substrates for the disposable articles of the present invention, can be premoistened with a emollient, lotion, tonic, disinfecting, sanitizing, or cleansing liquid, or other liquid suitable for application to an object intended to be treated. The liquid can be water or hydrophilic liquids (e.g., ethanol), as well as lipophilic liquids (silicones, hydrocarbons, oils, etc.).

The liquid can comprise, for example, a water soluble silicon based surfactant. In one embodiment, the lotion comprises an anionic silicon based sulfosuccinate surfactant.

Suitable counter ions include those derived from the alkaline metals (e.g. sodium, potassium); the alkaline earth metals (e.g. magnesium, calcium); ammonia, and alkanol amines (e.g. mono, di, and tri ethanol amines).

In one embodiment of the present invention, a lotion is provided comprising water and a silicon copolyol sulfosuccinate selected from the group consisting of disodium dimethicone copolyol sulfosuccinate and diammonium dimethicone copolyol sulfosuccinate.

The lotion preferably comprises less than about 1.00 percent by weight of the silicone based sulfosuccinate. In particular, the lotion can comprise less than about 0.20 percent by weight of the silicone based sulfosuccinate, and in embodiment comprises between about 0.08 and about 0.10 percent by weight of the silicone based sulfosuccinate. Preferably, the lotion comprises no more than about 1.00 percent by weight total surfactant solids, including the silicone based sulfosuccinate.

A suitable disodium dimethicone copolyol sulfosuccinate is commercially available as MACKANATE DC-30 and MACKANATE DC-50 brand sulfosuccinate surfactants available from the McIntyre Group, LTD, University Park, Ill. A suitable diammonium dimethicone copolyol sulfosuccinate is commercially available as MACKANATE DC-30A from the same supplier. U.S. Pat. No. 4,849,127 issued Jul. 18, 1989 to Maxon is incorporated herein by reference for its disclosure related to dimethicone copolyol sulfosuccinates.

The liquid used to premoisten the wipe can also comprise one or more of the following: an effective amount of a preservative, an effective amount of a humectant, an effective amount of an emollient; an effective amount of a fragrance, and an effective amount of a fragrance solubilizer.

As used herein, an emollient is a material that softens, soothes, supples, coats, lubricates, or moisturizes the skin. The term emollient includes, but is not limited to, conventional lipid materials (e.g. fats, waxes), polar lipids (lipids that have been hydrophylically modified to render them more water soluble), silicones, aloe extracts such as aloe vera, hydrocarbons, and other solvent materials. Emollients useful in the present invention can be petroleum based, fatty acid ester type, alkyl ethoxylate type, fatty acid ester ethoxylates, fatty alcohol type, polysiloxane type, mucopolysaccharides, or mixtures thereof Humectants are hygroscopic materials that function to draw water into the stratum corneum to hydrate the skin. The water may come from the dermis or from the atmosphere. Examples of humectants include glycerin, propylene glycol, and phospholipids.

Fragrance components, such as perfumes, include, but are not limited to water insoluble oils, including essential oils.

Fragrance solubilizers are components which reduce the tendency of the water insoluble fragrance component to precipitate from the lotion. Examples of fragrance solubilizers include alcohols such as ethanol, isopropanol, benzyl alcohol, and phenoxyethanol; any high HLB (HLB greater than 13) emulsifier, including but not limited to polysorbate; and highly ethoxylated acids and alcohols.

Preservatives prevent the growth of micro-organisms in the liquid lotion and/or the substrate. Generally, such preservatives are hydrophobic or hydrophillic organic molecules. Suitable preservatives include, but are not limited to parabens, such as methyl parabens, propyl parabens, and combinations thereof The liquid used to premoisten the wipe, or the wipe itself, can also comprise an effective amount of a kerotolytic for providing the function of encouraging healing of the skin. An especially preferred kerotolytic is Allantoin ((2,5-Dioxo-4-Imidazolidinyl)Urea), a heterocyclic organic compound having an empirical formula $C_4H_6N_4O_3$. Allantoin is commercially available from Tri-K Industries of Emerson, N.J.

U.S. Pat. No. 5,534,265 issued Jul. 9, 1996; U.S. Pat. No. 5,043,155 issued Aug. 27, 1991; and U.S. Pat. No. 5,648,083 issued Jul. 15, 1997 are incorporated herein by reference for the purpose of disclosing additional ingredients for use in a remoistened wipe. U.S. Pat. No. 4,904,524, issued Feb. 27, 1990, Yoh, discloses an alternative baby wipe comprising a planar substrate impregnated with an aqueous lotion and a hydrophobic functional ingredient (e.g., dimethicone) entrapped in polymeric beads (e.g. microsponges, microcapsules) concentrated near the surface of the substrate.

Wipes can also be made as described in U.S. Pat. No. 4,300,981 (Carstens, issued Nov. 17, 1981), U.S. Pat. No. 4,112,167 (Dake et al., issued Sep. 5, 1978), U.S. Pat. No. 4,481,243 (Allen; issued Nov. 6, 1984), U.S. Pat. No. 4,513,051 (Lavash; issued Apr. 23, 1985), and U.S. Pat. No. 5,840,403 (Trokhan et al.; issued Nov. 24, 1998), all hereby incorporated by reference.

Premoistened wipes can be made by wetting the dry substrate with, preferably, at least 1 gram of premoistening liquid per gram of dry fibrous web. Preferably, the dry substrate is wetted with at least about 2.0, and more preferably at least about 2.5 grams of liquid per gram of the dry fibrous web.

A wide variety of other devices and substrates can be used in conjunction with the responsive systems of the present invention. The material, form, and design will depend upon the type of article and its intended use. By way of example, non-limiting materials which can be used include sponges, closed cell foams, open cell foams, latex, rubber, polymeric materials (e.g., plastics, especially biodegradable plastics), wood, and absorbent webs (optionally containing superabsorbent polymeric gelling materials). In addition, the active ingredients described above for use in conjunction with the substrate of a wipe such as described above are not meant to be excluded from use as the active material of a responsive system, and such use is intended to be encompassed by the present invention.

Cleaning devices, such as mops, scrubbing devices, sponges, and the like are a preferred embodiment of the present invention. These include both wet-cleaning devices and dry-cleaning devices, the latter of which are suitable for cleaning objects without need for aqueous cleaning liquids, or if they do use aqueous cleaning liquids relatively small amounts are used. Such devices typically comprise a substrate which is reusable and a second, disposable substrate is disposed on or around the first substrate during use, or the entire, wherein the second substrate includes all or at least a part of the responsive system. Alternately, there is only a single substrate which, in which case said substrate includes all or at least a part of the responsive system. The disposable portion of the device also may include a wide variety of other materials to be used in treating an object, either as part of a responsive system or in a conventional manner. The devices may also include a wide variety of other structural components to assist with the treatment of functioning of the device. These elements will depend upon the design and end-use of the device and can be selected and utilized in accordance with the desires of one of ordinary skill in the art.

For example the present invention may comprise a body covering or a partial body covering such as a hand covering or glove which can treat the object in any manner as described herein. The hand cover can partially or wholly cover the hand. Body coverings or articles that partially cover the body or cover parts of the body are also contemplated. Preferably, the responsive system is generally located at or near at least a portion of the exterior surface: Example forms of handcovers include but are not limited to finger cots, gloves, mittens and hand wraps. Preferably, such body coverings are disposable. Such coverings may be used for medical care and assessment, zoological and veterinarian care, agricultural tasks associated with plant or livestock products, food preparation and handling both commercially and in-home either for intended consumption by humans or other living creatures.

Figure 12:
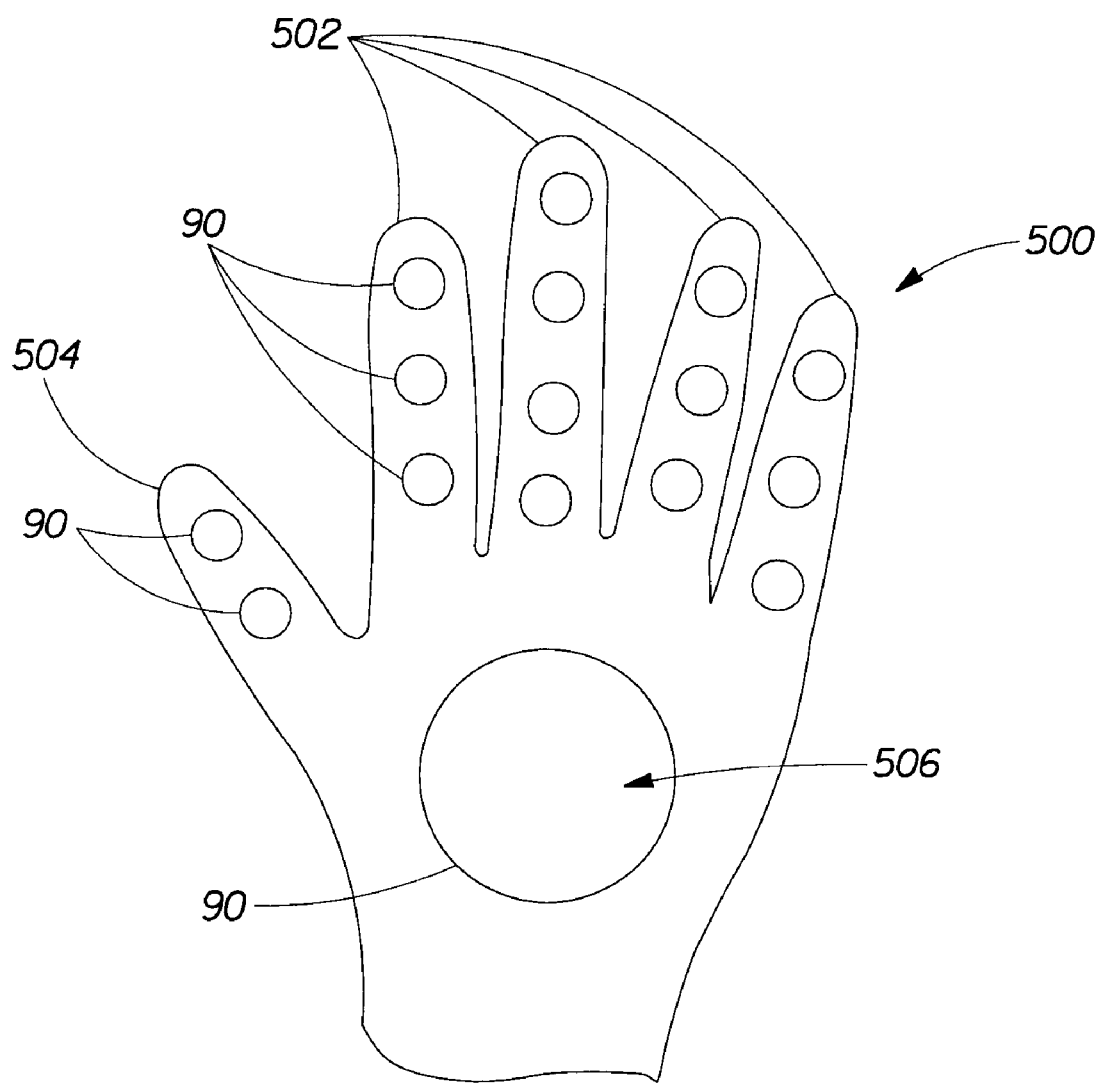
FIG. 12 shows a top view of an alternative embodiment of the present invention, wherein the article is a disposable glove.

In an embodiment shown in FIG. 12 is a disposable glove 500 having surface 508, fingers 502, thumb 504, and palm 506. The surface 508 can be constructed of a single layer of a woven or non-woven material, such as described above with respect to the planar substrate, but preferably is comprised of latex. Fingers 502, thumb 504, and palm 506 have disposed on the palm 506 side of the glove contaminant isolation devices such as the one described above, FIGS. 2 and 3, or other responsive systems (e.g., compression-active ingredient release devices as described above) though sized appropriately for proper fit onto the globe 500. Responsive system devices can also be positioned at any other location on the glove that may be desired, including without limitation the palm and back of the palm.

Other forms of body apparel are also encompasses, such as but not limited to mittens, and socks. For example shoes and socks can be designed to sense perspiration and release via the actuator an antiperspirant or activate a perspiration isolation device or absorbent web.

Figure 13A:
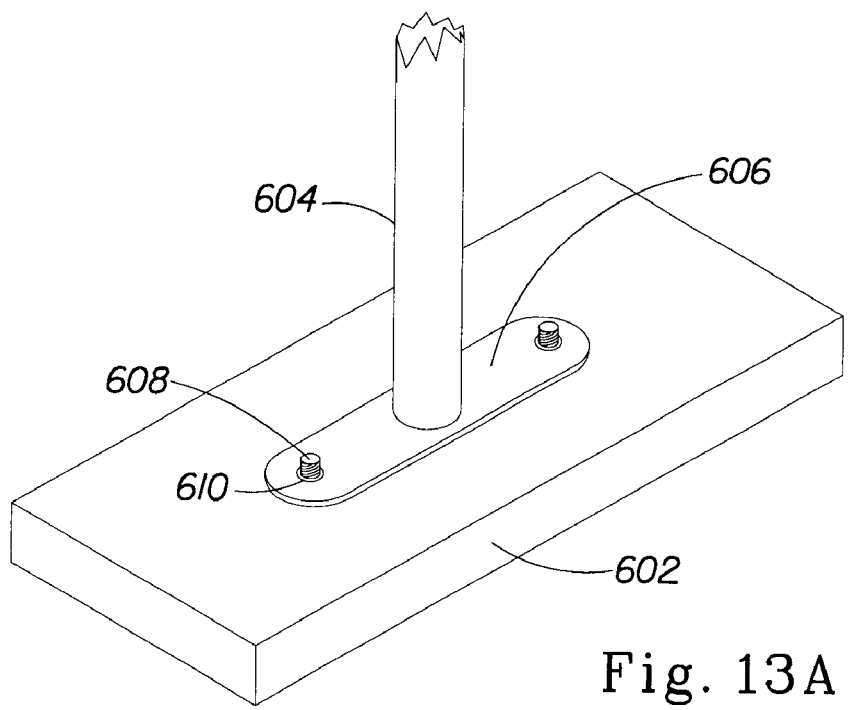
FIGS. 13A and 13B show another embodiment of the present invention, wherein the article shown is a mop with a disposable mop head.
Figure 13B:
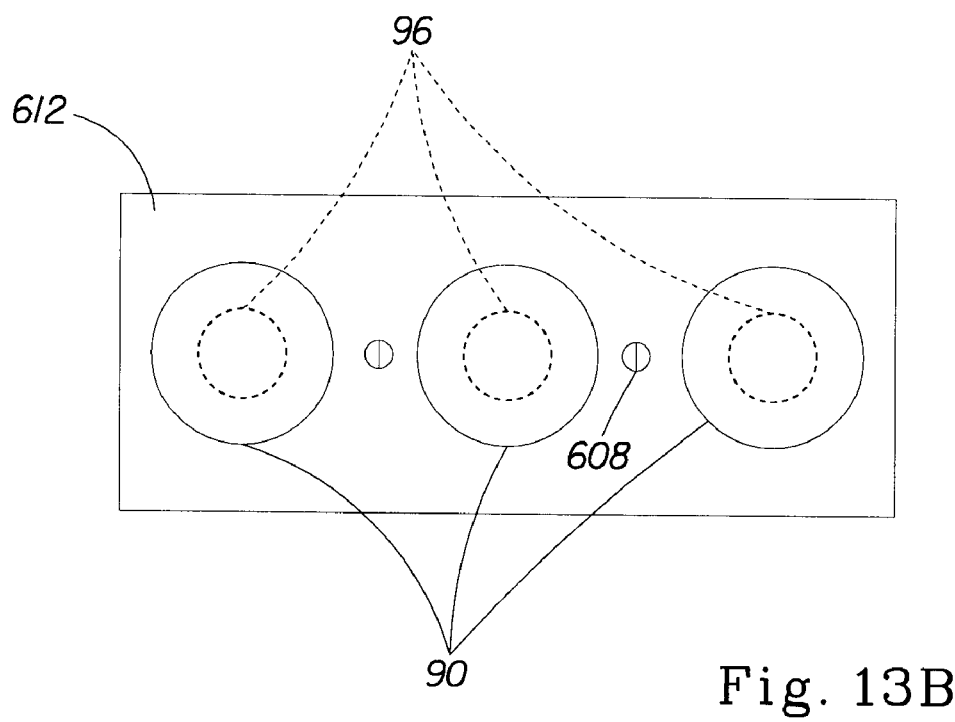

In another preferred embodiment, such as exemplified in FIG. 13, provided is a disposable mop 600 having a responsive system wherein the mop 600 comprises an elongated handle 604 and a mop head 602 connected to one end of the elongated handle 604 via a bracket 606. In this embodiment the mop head is disposable, and the substrate of the mop head is made of a biodegradable material, such as a non-woven fibrous web. Bracket 606 has threaded orifices 610 through which screws 608 extending upward through mop head 602, thereby securing the mop head to the bracket. The elongated handle 604 can be connected to the bracket 606 by any suitable means as will be known in the art, such as by screwing into the bracket, nails, staples, glue, etc. Referring to FIG. 13B, shown is the bottom surface 612 of the mop head 602, which is the portion of the mop head which would typically contact the surface to be treated during normal use. Bottom surface 612 has contaminant isolation devices 90, such as disclosed in FIGS. 2 and 3. Screws 608 extend from the mop head 602 upward toward the bracket 606 where they are affixed in place by threaded orifices 610. Preferably screws 608 are recessed into the mop head 602 so they do not contact the surface to be treated.

Figure 14A:
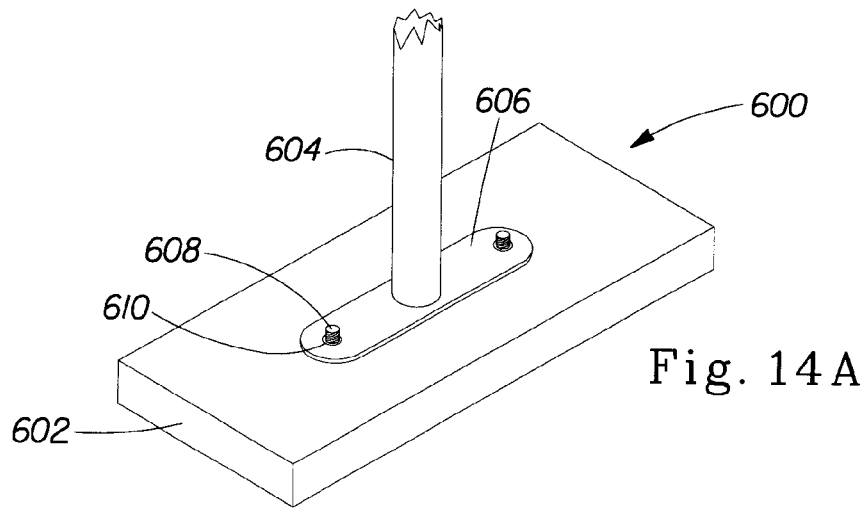
FIGS. 14A, 14B, and 14C show another embodiment of the present invention, wherein the article shown is a mop with a disposable mop head cover.
Figure 14B:
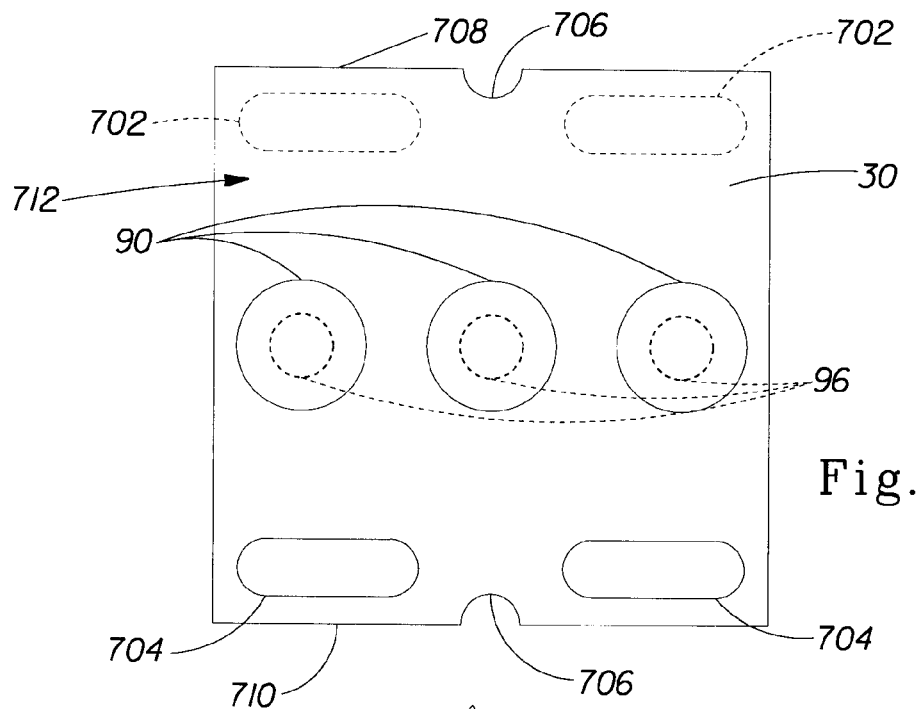
Figure 14C:
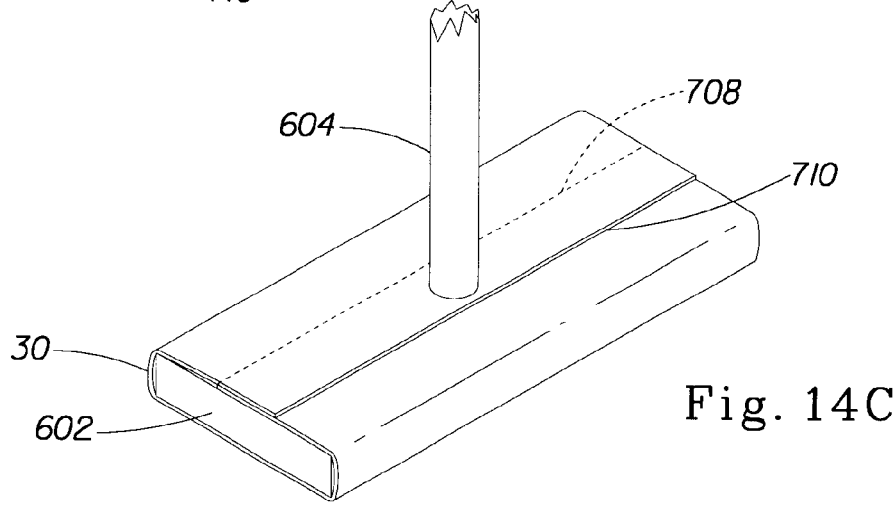

FIG. 14 shows yet another disposable mop embodiment. FIG. 14A is similar to FIG. 13A, except now referring to FIG. 14B, a disposable mop head cover 700 is provided which fits mop head 602. Mop head cover 700 is made from a planar substrate, such as previously described but in this embodiment preferably a polymeric closed cell or open cell foam, and further has first edge 708, second edge 710, outward face 712 having contaminant isolation devices 90 attached, for example attached with glue. Mop head cover 700 wraps around mop head 602 as shown in FIG. 14C with first edge 708 overlapping second edge 710 and is held in place by the hook portion of hook and loop fasteners 702, located near the first edge 708 on the opposite face of the substrate from the outer face 712, and loop portion of hook and loop fasteners 704, located near the second edge 710 on the outer face 712. Handle orifices 706 facilitate good fit around the handle 604.

Planar substrates which are suitable for use with the present invention, and especially for cleaning devices such as a dry mop, are more fully described in U.S. patent application Ser. No. 09/082,349 entitled "Novel Structures Useful As Cleaning Sheets", filed May 20, 1998; and U.S. patent application Ser. No. 09/082,396 entitled "Novel Three Dimensional Structures Useful As Cleaning Sheets", filed May 20, 1998, both of which are hereby incorporated herein by reference. While the above-described sheets are preferred, it will be understood that others may be equal suitable for use with the present invention.

While particular non-limiting embodiments and examples of the present invention have been illustrated and described, it would be obvious to those skilled in the art that various other changes and modifications can be made without departing from the spirit and scope of the invention. For example, although the present invention is illustrated and described primarily with respect to a disposable diaper, the present invention is not limited to this embodiment. It :is therefore intended to cover in the appended claims all such changes and modifications that are within the scope of this invention.

What is claimed is:

1. A disposable article suitable for treating an object comprising a responsive system including:
   (i) a sensor operatively connected to said article, said sensor being adapted to detect an input, and
   (ii) an actuator operatively connected to said sensor, said actuator being adapted to perform a responsive function upon said input, said actuator comprising a distinct component from said sensor.

2. The disposable article of claim 1, wherein said responsive system further comprises a feedback control loop in which said controller is adapted to allow said actuator to perform said responsive function upon said input when said sensor detects said input.

3. The disposable article of claim 1, wherein said actuator performs said responsive function in a continuous manner.

4. The disposable article of claim 1, wherein said actuator performs said responsive function in a discontinuous manner.

5. The disposable article of claim 4, wherein said discontinuous responsive system comprises a step-type responsive system.

6. The disposable article of claim 4, wherein said discontinuous responsive function is performed such that said discontinuous responsive system has an output function that may be modeled by the equation:

$$\left.\frac{dR}{dI}\right|_{I=I_0} = k\frac{(\Delta R_T)}{(\Delta I_T)},$$

wherein said constant k is greater than or equal to a value selected from the group of about 2.0, about 3.0, about 5.0, about 10.0 and about 100.

7. The disposable article of claim 4, wherein said discontinuous responsive function is performed such that said discontinuous responsive system has an output function that may be modeled by a control system having a transfer function of the equation: $KG(s)=K/(Ts+1)^n$, wherein said n value is greater than or equal to a value selected from the group of: about 25, about 50 and about 100.

8. The disposable article of claim 1 further comprising a controller, said controller being adapted to receive a signal from said sensor and allow said actuator to perform said responsive function when said sensor detects said input.

9. The disposable article of claim 8, wherein said controller is a distinct component from said sensor and said actuator.

10. The disposable article of claim 1, wherein said feedback control loop is selected from the group consisting of: a modulating feedback control loop and a non-modulating feedback control loop.

11. The disposable article of claim 1 further comprising a second sensor, said second sensor is adapted to detect a second input.

12. The disposable article of claim 11, wherein said actuator is adapted to perform said responsive function when said sensor detects said input or said second sensor detects said second input.

13. The disposable article of claim 1, wherein said responsive function comprises one or more of the group selected from transforming potential energy into kinetic energy, delivering a material, removing a material, and isolating a material.

14. The disposable article of claim 1, wherein said actuator is adapted, to transform a potential energy in order to perform said responsive function, said potential energy being selected from one or more of the group of stored mechanical energy, compressive mechanical energy, torsional mechanical energy, stored chemical energy, stored electrical energy, and a battery.

15. The disposable article of claim 14, wherein said actuator delivers one or more active ingredient selected from the group consisting of antimicrobials, antifungals, biologically active agents, physiologically active agents, chemical reactants, pH buffers, pH modifiers, cleaning agents, conditioning agents, cosmetics, drugs, absorbent materials, and rheology modifiers.

16. The disposable article of claim 15 wherein said active ingredient is selected from one or more of the group consisting of enzyme inhibitors and fecal modifying agents.

17. The disposable article according to claim 1, wherein the actuator comprises an isolation device.

18. The disposable article of claim 1, wherein said sensor is selected from the group of an electrical sensor, a mechanical sensor, a chemical sensor, a biosensor, and a closed system liquid transport member.

19. The disposable article of claim 1, wherein said actuator is selected from the group of: an electrical pump, an electrically sensitive gel, and an electrically activated valve.

20. The disposable article of claim 1, wherein said input is selected from the group of water, pH, electrical activity, a microorganism, and an enzyme.

21. The disposable article of claim 1, wherein said article is a cleaning article.

22. The disposable article of claim 1, wherein said article further comprises a planar substrate, wherein said responsive system is disposed on or incorporated into said substrate.

23. The disposable article of claim 1, wherein said article is selected from the group consisting of, tissues, towels, wipes, sponges, mops, and gloves.

24. The disposable article of claim 1, wherein said sensor is proactive.

25. The disposable article of claim 1 further comprising a controller, said controller being adapted to receive a signal from said sensor and allow said actuator to perform said responsive function when a threshold level of said input has been met.

26. A disposable article suitable for treating an object comprising:
(a) a responsive system including:
(i) a sensor operatively connected to said article, said sensor being adapted to detect an input, and
(ii) an actuator operatively connected to said sensor, said actuator being adapted to perform a responsive function upon said input, said actuator comprising a distinct component from said sensor; and
(b) a substrate, wherein at least a part of said responsive system is operatively connected to said substrate.

27. A disposable article according to claim 26 wherein said substrate is a planar substrate.

28. A disposable article according to claim 26 wherein said responsive system is discontinuous.

29. A disposable article suitable for treating an object comprising:
(a) a responsive system including:
(i) a sensor operatively connected to said article, said sensor being adapted to detect an input, and
(ii) an actuator operatively connected to said sensor, said actuator being adapted to perform a responsive function upon said input, said actuator comprising a distinct component from said sensor; and
(b) a substrate, wherein at least a part of said responsive system is operatively connected to said substrate;
wherein said responsive system comprises compression material in a compressed state prior to and upon actuation forms a three dimensional structure.

30. A disposable article according to claim 29, wherein said three dimensional structure formed is suitable for isolating a material.

31. A disposable article suitable for treating an object comprising:
(a) a responsive system including:
(i) a sensor operatively connected to said article, said sensor being adapted to detect an input, and
(ii) an actuator operatively connected to said sensor, said actuator being adapted to perform a responsive function upon said input, said actuator comprising a distinct component from said sensor; and
(b) a substrate, wherein at least a part of said responsive system is operatively connected to said substrate;
wherein said actuator further comprises a treatment material for treating said object, whereby said treatment material is released upon actuation of the responsive system.

32. A disposable article according to claim 31, wherein said actuator comprises a compression material and treatment material disposed on in said compression material, whereby upon actuation said compression material releases said treatment material.

33. A disposable article according to claim 29 wherein said responsive system is discontinuous.

34. A disposable article according to claim 31 wherein said responsive system is discontinuous.

* * * * *